US009598390B2

(12) United States Patent
Shi et al.

(10) Patent No.: US 9,598,390 B2
(45) Date of Patent: Mar. 21, 2017

(54) BICYCLO[2.2.2]ACID GPR120 MODULATORS

(71) Applicant: BRISTOL-MYERS SQUIBB COMPANY, Princeton, NJ (US)

(72) Inventors: Yan Shi, Flourtown, PA (US); Hao Zhang, Belle Mead, NJ (US); Peter T. W. Cheng, Princeton, NJ (US); Shiwei Tao, Hillsborough, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/774,276

(22) PCT Filed: Mar. 13, 2014

(86) PCT No.: PCT/US2014/025187
§ 371 (c)(1),
(2) Date: Sep. 10, 2015

(87) PCT Pub. No.: WO2014/159802
PCT Pub. Date: Oct. 2, 2014

(65) Prior Publication Data
US 2016/0039780 A1    Feb. 11, 2016

Related U.S. Application Data

(60) Provisional application No. 61/782,396, filed on Mar. 14, 2013.

(51) Int. Cl.

| | | |
|---|---|---|
| *C07C 59/72* | (2006.01) | |
| *C07D 307/79* | (2006.01) | |
| *C07C 255/54* | (2006.01) | |
| *C07D 231/12* | (2006.01) | |
| *A61K 31/192* | (2006.01) | |
| *A61K 31/415* | (2006.01) | |
| *A61K 31/343* | (2006.01) | |
| *A61K 31/277* | (2006.01) | |
| *A61K 45/06* | (2006.01) | |

(52) U.S. Cl.
CPC .......... *C07D 307/79* (2013.01); *A61K 31/192* (2013.01); *A61K 31/277* (2013.01); *A61K 31/343* (2013.01); *A61K 31/415* (2013.01); *A61K 45/06* (2013.01); *C07C 59/72* (2013.01); *C07C 255/54* (2013.01); *C07D 231/12* (2013.01); *C07C 2102/44* (2013.01)

(58) Field of Classification Search
CPC .... C07D 307/79; C07D 231/12; C07C 59/72; C07C 255/54; C07C 2102/44
USPC ....... 548/376.1; 549/462; 558/414; 562/502; 514/406, 469, 522, 569
See application file for complete search history.

(56) References Cited

U.S. PATENT DOCUMENTS

| | | | | |
|---|---|---|---|---|
| 6,008,234 | A | * 12/1999 | Kochanny | C07D 401/12 514/328 |
| 6,649,600 | B1 | * 11/2003 | Kiesman | C07D 473/06 514/263.22 |
| 8,962,660 | B2 | 2/2015 | Zhang et al. | |
| 2004/0259889 | A1 | * 12/2004 | Smits | A61K 31/00 514/263.33 |
| 2005/0203065 | A1 | * 9/2005 | Smits | C07D 473/06 514/81 |
| 2010/0056553 | A1 | * 3/2010 | Plettenburg | C07D 217/24 514/278 |

FOREIGN PATENT DOCUMENTS

| | | | | |
|---|---|---|---|---|
| EP | 1712547 A1 | 10/2006 | | |
| WO | WO 0134610 A1 | * 5/2001 | ........... | C07D 473/06 |
| WO | WO2007/071966 A1 | 6/2007 | | |
| WO | WO2013/068328 A1 | 5/2013 | | |
| WO | WO 2013068328 A1 | * 5/2013 | ........... | C07D 403/04 |
| WO | WO 2013074387 A1 | * 5/2013 | ........... | C07D 401/14 |

OTHER PUBLICATIONS

U.S. Appl. No. 14/774,289, filed Sep. 10, 2015, Bristol-Myers Squibb Company.

* cited by examiner

*Primary Examiner* — Michael Barker
*Assistant Examiner* — Amanda L Aguirre
(74) *Attorney, Agent, or Firm* — Elliott Korsen; Jing G. Sun

(57) ABSTRACT

The present invention provides compounds of Formula (I) or a stereoisomer, or a pharmaceutically acceptable salt thereof, wherein all of the variables are as defined herein. These compounds are GPR120 G protein-coupled receptor modulators which may be used as medicaments.

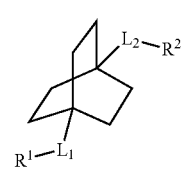

(I)

9 Claims, No Drawings

BICYCLO[2.2.2]ACID GPR120 MODULATORS

CROSS-REFERENCE TO RELATED APPLICATIONS

This application claims priority to U.S. Provisional Application Ser. No. 61/782,396, filed Mar. 14, 2013; the entire content of which is incorporated herein by reference.

FIELD OF THE INVENTION

The present invention provides novel bicyclo[2.2.2] compounds, and their analogues thereof, which are GPR120 G protein-coupled receptor modulators, compositions containing them, and methods of using them, for example, for the treatment of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Polyunsaturated fatty acids (PUFAs) such as omega-3 fatty acids are known to improve sensitivity to insulin. Insulin sensitivity can be improved by exerting anti-inflammatory effects in monocytes and/or macrophages and/or by enhancing glucose uptake in adipose and muscle. GPR120 is a membrane-bound receptor responsive to PUFAs which is preferentially expressed in adipose tissue and monocytes/macrophages. To decrease the medical burden of type 2 diabetes through enhanced glycemic control, GPR120 modulator compounds hold the promise of exerting a sensitizing effect to insulin as well as potential combination with a broad range of anti-diabetic drugs.

The present invention relates to novel substituted bicyclic acid compounds which have the ability to modulate GPR120. Such compounds are therefore potentially useful for the treatment or prophylaxis of diabetes and related conditions.

SUMMARY OF THE INVENTION

The present invention provides bicyclo[2.2.2] compounds, and their analogues thereof, which are useful as GPR120 modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment of multiple diseases or disorders associated with GPR120, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR120.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

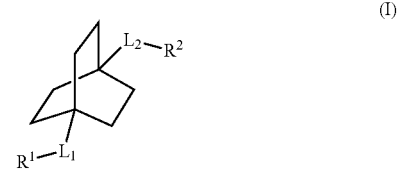

or a stereoisomer, a tautomer, a pharmaceutically acceptable salt, or a solvate thereof, wherein:

$L_1$ is independently $L_4$-O or O-$L_4$;

$L_2$ is independently a hydrocarbon linker substituted with 0-2 $R^c$ or a hydrocarbon-heteroatom linker substituted with 0-2 $R^c$; wherein said hydrocarbon linker has one to six carbon atoms and may be straight or branched, saturated or unsaturated; and said hydrocarbon-heteroatom linker has one to four carbon atoms and one group selected from O, —CO—, S, —SO—, —SO$_2$—, NH and N($C_{1-4}$ alkyl);

$L_4$ is independently a bond or a hydrocarbon linker; wherein said hydrocarbon linker has one to four carbon atoms and may be straight or branched;

$R^1$ is independently selected from: $C_{6-10}$ carbocycle and a 5- to 10-membered heterocycle comprising carbon atoms and 1-4 heteroatoms selected from N, NR$^b$, O, and S(O)$_p$; wherein said carbocycle and heterocycle are substituted with 0-4 $R^3$ and 0-1 $R^4$;

$R^2$ is independently selected from: CO$_2$H and —CONHSO$_2$($C_{1-4}$ alkyl);

$R^3$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, and NO$_2$;

$R^4$ is independently -$L_3$-$R^5$;

$L_3$ is independently selected from: a bond, O, and C(=O);

$R^5$ is independently selected from: phenyl and a 5- to 6-membered heteroaryl comprising carbon atoms and 1-4 heteroatoms selected from N, NR$^b$, O, and S(O)$_p$; wherein each ring moiety is substituted with 0-2 $R^a$;

$R^a$, at each occurrence, is independently selected from: halogen, $C_{1-4}$ alkyl, $C_{1-4}$ alkoxy, and $C_{1-4}$ haloalkyl;

$R^b$, at each occurrence, is independently selected from: H, $C_{1-4}$ alkyl, and —(CH$_2$)$_{0-2}$-(phenyl substituted with 0-3 $R^d$);

$R^c$, at each occurrence, is independently selected from: halogen, OH, $C_{1-4}$ alkyl, $C_{1-4}$ haloalkyl, and $C_{1-4}$ alkyoxy;

$R^d$, at each occurrence, is independently selected from: halogen, $C_{1-4}$ alkyl, $C_{1-4}$ alkoxy, and $C_{1-4}$ haloalkyl; and p is, independently at each occurrence, selected from 0, 1, and 2.

In a second aspect, the present invention includes a compound of Formula (I) or a stereoisomer, a tautomer, a pharmaceutically acceptable salt, or a solvate thereof, within the scope of the first aspect, wherein:

$L_1$ is independently $L_4$-O or O-$L_4$;

$L_2$ is independently a hydrocarbon linker substituted with 0-1 $R^c$ or a hydrocarbon-heteroatom linker substituted with 0-1 $R^c$; wherein said hydrocarbon linker has one to six carbon atoms and may be straight or branched, saturated or unsaturated; and said hydrocarbon-heteroatom linker has one to four carbon atoms and one group selected from O, —CO— and S;

$R^1$ is independently selected from: phenyl, indanyl, naphthyl, and a 5- to 10-membered heterocycle comprising carbon atoms and 1-4 heteroatoms selected from N, $NR^b$, O, and $S(O)_p$; wherein each ring moiety substituted with 0-4 $R^3$ and 0-1 $R^4$; and $R^4$ is independently selected from: thienyl, oxadiazolyl, and -$L_3$-phenyl; wherein each ring moiety is substituted with 0-2 $R^a$.

In a third aspect, the present invention includes a compound of Formula (II):

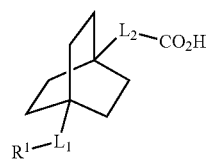

(II)

or a stereoisomer, a tautomer, a pharmaceutically acceptable salt, or a solvate thereof, within the scope of the first or second aspect, wherein:

$L_1$ is independently $L_4$-O or O-$L_4$;

$L_2$ is independently a hydrocarbon linker or a hydrocarbon-heteroatom linker;

wherein said hydrocarbon linker has one to five carbon atoms and may be straight or branched, saturated or unsaturated; and said hydrocarbon-heteroatom linker has one to five carbon atoms and may be straight or branched, and has one to three carbon atoms and one O;

$L_4$ is independently a bond or $CH_2$;

$R^1$ is independently selected from:

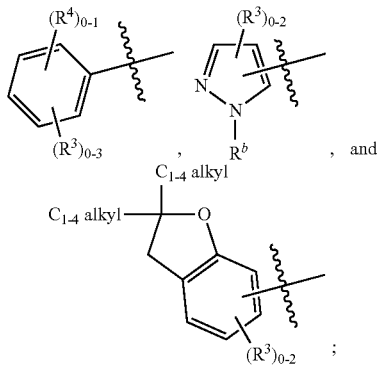

$R^3$, at each occurrence, is independently selected from: $NO_2$, halogen, $C_{1-4}$ alkyl, $C_{1-4}$ alkoxy, $C_{1-4}$ alkylthio, $C_{1-4}$ haloalkyl, $C_{1-4}$ haloalkoxy, and $C_{1-4}$ haloalkylthio;

$R^4$ is independently selected from: thienyl, oxadiazolyl, and -$L_3$-phenyl; wherein each ring moiety is substituted with 0-2 $R^a$;

$L_3$ is independently a bond, O or C(=O);

$R^a$, at each occurrence, is independently selected from: halogen and $C_{1-4}$ alkyl; and $R^b$ is independently phenyl substituted with 0-2 halo.

In a fourth aspect, the present invention includes a compound of Formula (I) or (II), or a stereoisomer, a tautomer, a pharmaceutically acceptable salt, or a solvate thereof, within the scope of any of the above aspects, wherein:

$L_2$ is independently selected from: $CH_2CH_2$, $CH_2CH_2CH_2$, CH=CH, $CH_2OCH_2$; and $R^1$ is independently selected from:

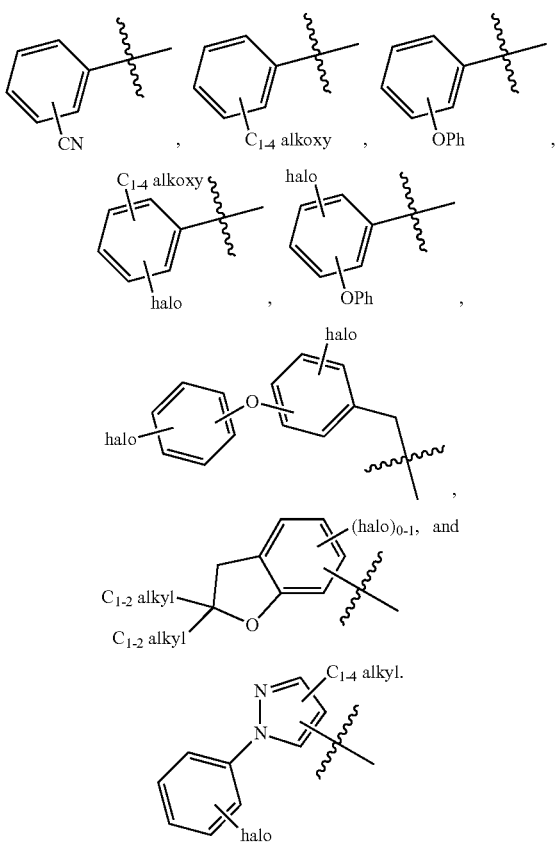

In a fifth aspect, the present invention includes a compound of Formula (I) or (II), or a stereoisomer, a tautomer, a pharmaceutically acceptable salt, or a solvate thereof, within the scope of any of the above aspects, wherein:

$R^1$-$L_1$- is independently selected from:

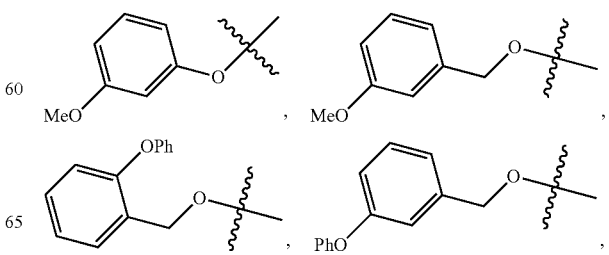

-continued

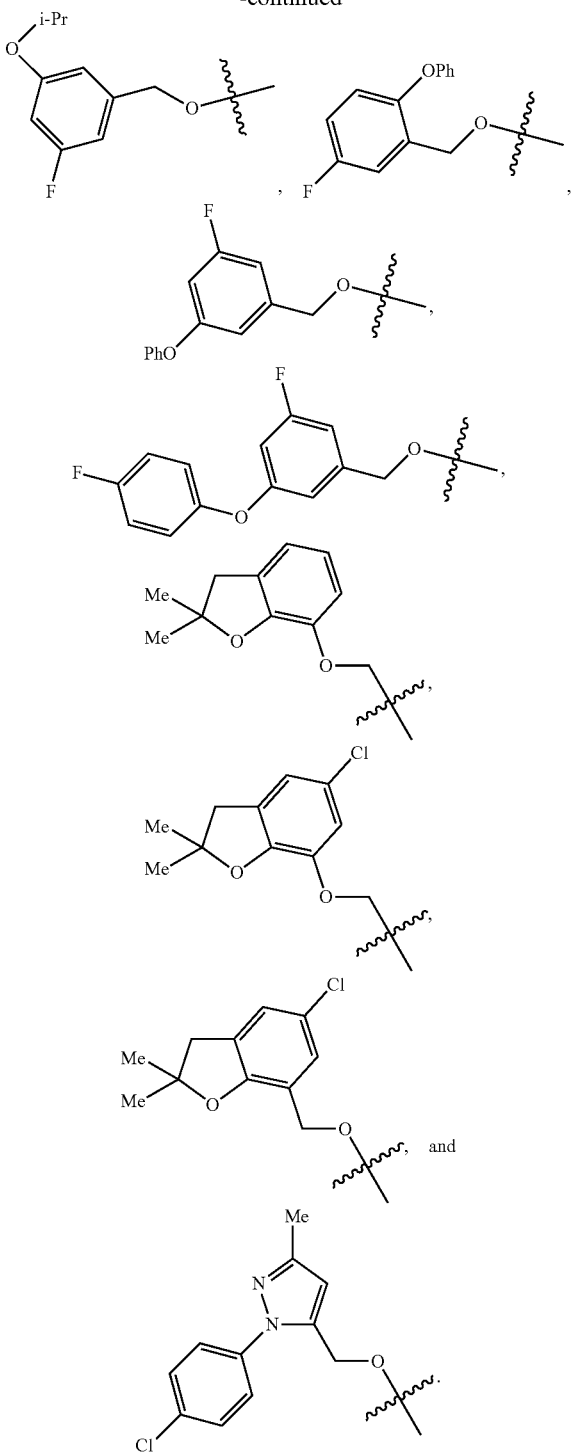

In a sixth aspect, the present invention provides a compound selected from the exemplified examples within the scope of the first aspect, or a stereoisomer, a tautomer, a pharmaceutically acceptable salt, or a solvate thereof.

In another aspect, the present invention provides a compound selected from any subset list of compounds within the scope of any of the above aspects.

In another aspect, $R^1$ is independently phenyl substituted with 0-4 $R^3$ and 0-1 $R^4$.

In another embodiment, the compounds of the present invention have hGPR120 $EC_{50}$ values ≤10 μM.

In another embodiment, the compounds of the present invention have hGPR120 $EC_{50}$ values ≤5 μM.

In another embodiment, the compounds of the present invention have hGPR120 $EC_{50}$ values ≤1 μM.

In another embodiment, the compounds of the present invention have hGPR120 $EC_{50}$ values ≤0.5 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin and alogliptin), a sodium-glucose transporter-2 (SGLT2) inhibitor (for example a member selected from dapagliflozin, canagliflozin, empagliflozin and remagliflozin), a GPR40/FFAR1 (Free fatty acid receptor 1) agonist (for example, TAK-875), and/or an MGAT2 (monoacylglycerol transferase 2) inhibitor (for example, compounds from WO 2012/124744, or compound (S)-10 from *Bioorg. Med. Chem. Lett.* (2013), doi: http://dx.doi.org/10.1016/j.bmcl.2013.02.084).

In a preferred embodiment, the present invention provides pharmaceutical composition, wherein the additional therapeutic agents are, for example, a dipeptidyl peptidase-IV inhibitor, a sodium-glucose transporter-2 inhibitor and an 11b-HSD-1 inhibitor.

In another embodiment, the present invention provides a method for the treatment of multiple diseases or disorders associated with GPR120, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the GPR120 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis.

In another embodiment, the present invention provides a method for the treatment of diabetes, hyperglycemia, gestational diabetes, obesity, dyslipidemia and hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with GPR120.

In another embodiment, the present invention also provides the use of a compound of the present invention for the manufacture of a medicament for the treatment of multiple diseases or disorders associated with GPR120.

In another embodiment, the present invention provides a method for the treatment of multiple diseases or disorders associated with GPR120, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, linagliptin, vildagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with GPR120.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR120 receptor modulator of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin, alogliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, peliglitazar, tesaglitazar and aleglitazar), glucokinase activators (for example, PF-04937319 and AMG-151), GPR119 receptor modulators (for example, MBX-2952, PSN821, and APD597), sodium-glucose transporter-2 (SGLT2) inhibitors (for example, dapagliflozin, canagliflozin, empagliflozin and remagliflozin), GPR40 receptor agonists (e.g., TAK-875), amylin analogs such as pramlintide, and/or insulin.

The GPR120 receptor modulator of the present invention may also be optionally employed in combination with agents for treating complication of diabetes. These agents include PKC inhibitors and/or AGE inhibitors.

The GPR120 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 inhibitors and the like. The GPR120 receptor modulator of the present invention may also be employed in combination with an agonist of the glucagon-like peptide-1 receptor (GLP-1 R), such as exenatide, liraglutide, GLP-1(1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2+}$) ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984);

f) Rautio, J. et al., *Nature Rev. Drug Discovery*, 7: 255-270 (2008), and g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography and mass spectrometry, "HPLC" for high pressure liquid chromatography, "[M−H]" for parent mass minus a proton, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$Ag_2CO_3$ silver carbonate
AgOAc silver acetate
AgOTf silver triflate
$CDCl_3$ deutero-chloroform
$CHCl_3$ chloroform
cDNA complimentary DNA
DMF dimethyl formamide
DMSO dimethyl sulfoxide
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
HCl hydrochloric acid
$H_2SO_4$ sulfuric acid
$K_2CO_3$ potassium carbonate
KCN potassium cyanide
mCPBA or m-CPBA meta-chloroperbenzoic acid
Pd/C palladium on carbon
$PhSO_2Cl$ benzenesulfonyl chloride
i-$Pr_2NEt$ diisopropylethylamine
PS polystyrene
$SiO_2$ silica oxide/silica gel
$SnCl_2$ tin(II) chloride
TEA triethylamine
TFA trifluoroacetic acid
TFAA trifluoroacetic anhydride
THF tetrahydrofuran
$TMSCHN_2$ trimethylsilyldiazomethane
KOAc potassium acetate
$MgSO_4$ magnesium sulfate
MsCl methanesulfonyl chloride
MsOH or MSA methylsulfonic acid
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Synthesis*, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*, Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

The general synthesis of compounds of Formula 1a and 1b are described in Scheme 1. The alcohol 3 is alkylated with alkyl halide 2 using silver triflate or silver oxide-mediated conditions (Burk et al., *Tetrahedron Lett.*, 35:8111 (1994)), followed by hydrolysis with a base (i.e., 1 N NaOH or 1 N LiOH) to afford the acid 1a. Alternatively, the alcohol 3 can be alkylated under Mitsunobu reaction conditions (e.g., Swamy, K. et al., *Chem. Rev.*, 109:2551 (2009)) and then base hydrolysis to provide compound 1b as also shown in Scheme 1.

*Chem.*, 47:2951 (1982)) with $BH_3$-THF provides the corresponding alcohol, which is treated with Dess-Martin periodinane to afford the iodide aldehyde 7. Wittig reaction with methyl 2-(triphenylphosphoranylidene)acetate and then hydrogenation affords the ester 8. The methyl ether in 8 is then converted to the diester 9 using $Ac_2O$ and $BF_3 \cdot OEt_2$. Basic hydrolysis of 9 provides the corresponding carboxylic acid, which is esterified to afford the alcohol intermediate 3a or 3b.

The ester 8 can also be converted to the cyanide 10 in a three-step sequence (reduction to its alcohol, conversion to its mesylate and then sodium cyanide treatment). The methyl ether in 10 is then converted to an ester (demethylation followed by acetylation) under $Ac_2O/BF_3 \cdot OEt_2$ conditions, followed by final base hydrolysis to provide the intermediate 3c.

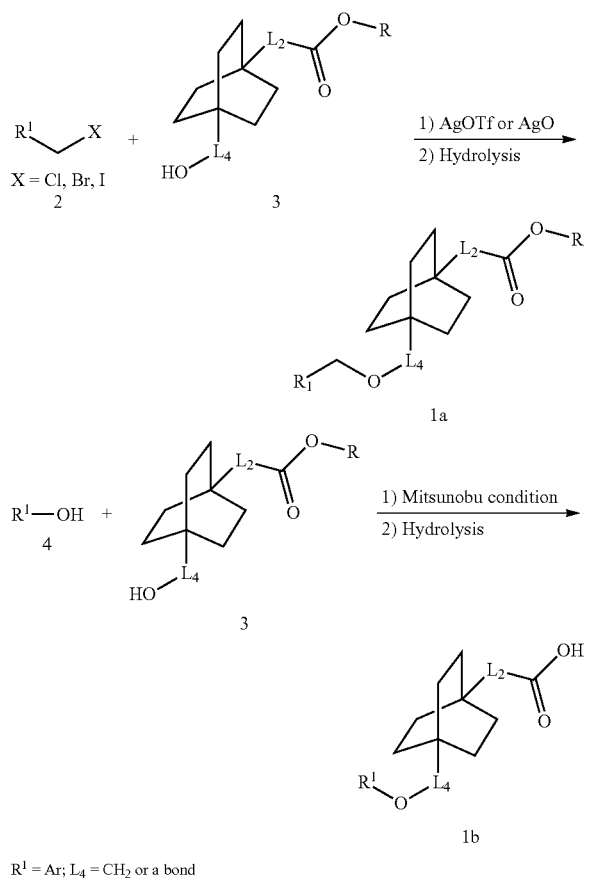

Scheme 1

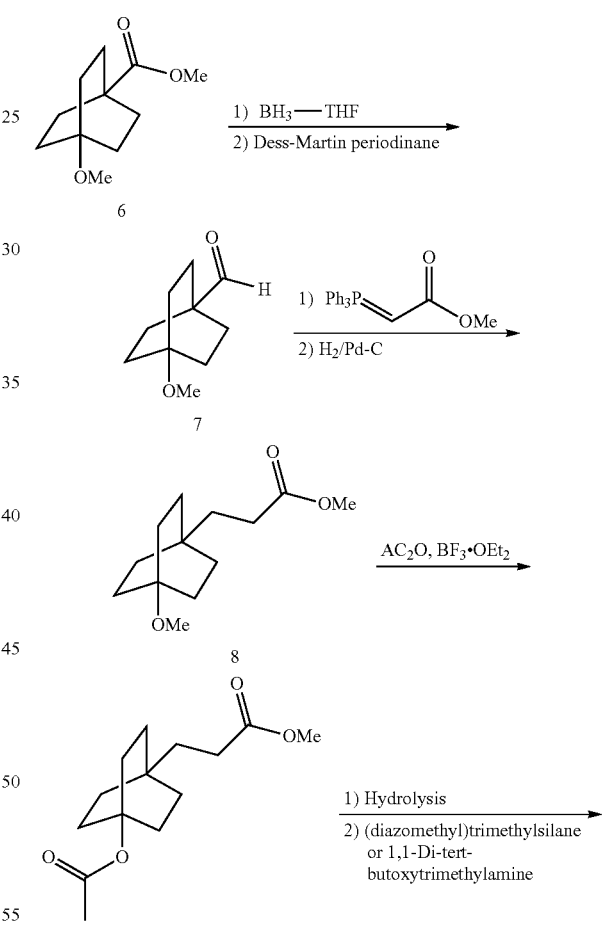

Scheme 3

The alkyl halides 2 are either commercially available or can be prepared from their corresponding alcohols according to literature procedures. Scheme 2 depicts a typical method to synthesize the alkyl halide 2.

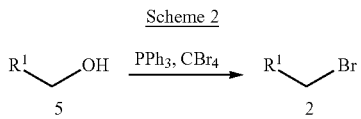

Scheme 2

Schemes 3 and 4 illustrated the syntheses of the intermediate alcohol 3. Reduction of acid 6 (Adcock et al., *J. Org.*

-continued

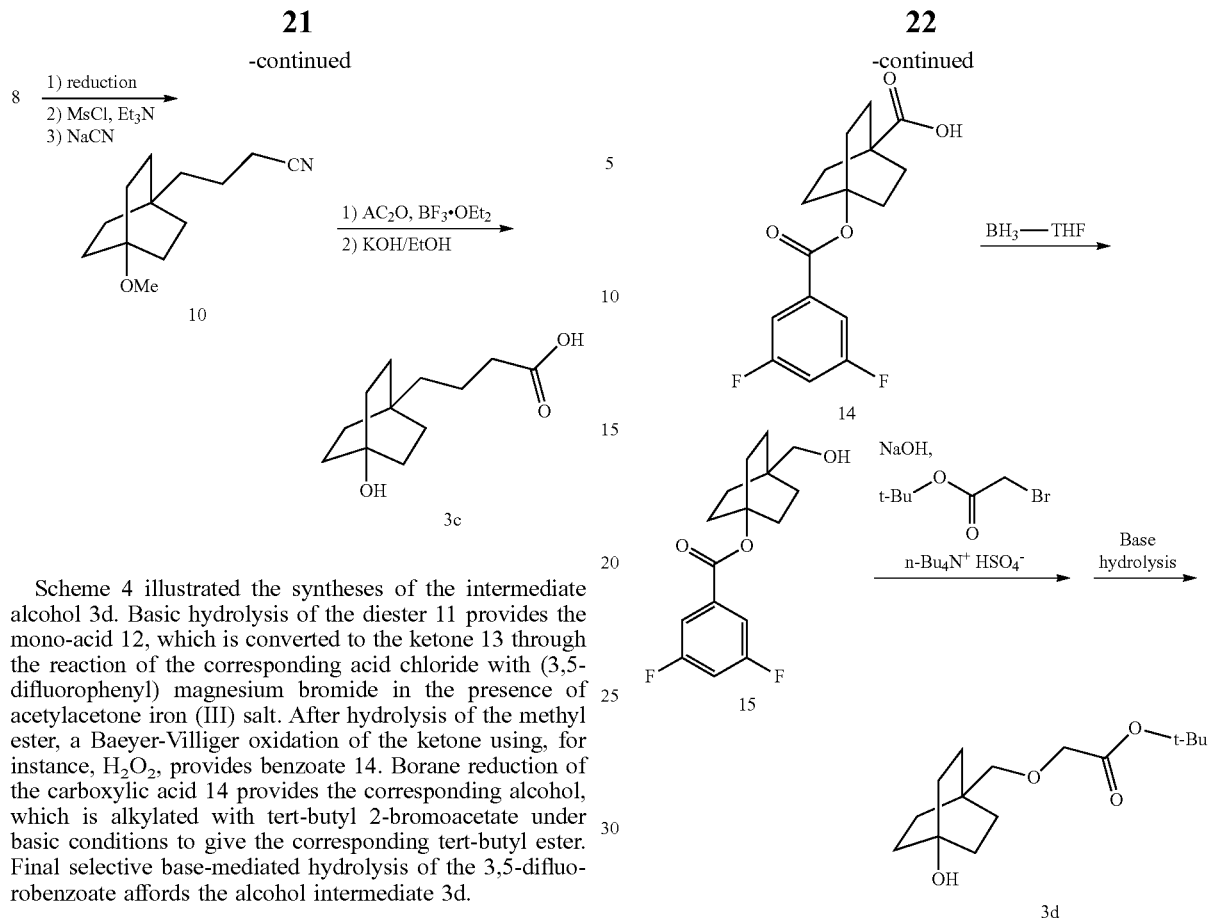

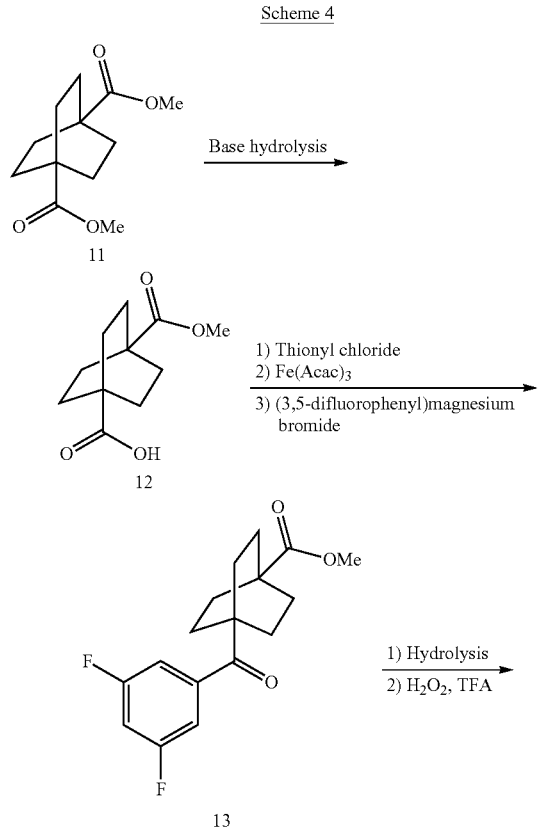

Scheme 4 illustrated the syntheses of the intermediate alcohol 3d. Basic hydrolysis of the diester 11 provides the mono-acid 12, which is converted to the ketone 13 through the reaction of the corresponding acid chloride with (3,5-difluorophenyl) magnesium bromide in the presence of acetylacetone iron (III) salt. After hydrolysis of the methyl ester, a Baeyer-Villiger oxidation of the ketone using, for instance, $H_2O_2$, provides benzoate 14. Borane reduction of the carboxylic acid 14 provides the corresponding alcohol, which is alkylated with tert-butyl 2-bromoacetate under basic conditions to give the corresponding tert-butyl ester. Final selective base-mediated hydrolysis of the 3,5-difluorobenzoate affords the alcohol intermediate 3d.

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Recently, five GPCRs (FFAR1 (GPR40), FFAR2 (GPR43), FFAR3 (GPR41), GPR84, and GPR120) were reported to recognize free fatty acids FFAR1, recognizes medium-long chain fatty acids like palmitic acid and linoleic acid FFAR2 and FFAR3 recognize short-chain fatty acids like acetate and butyrate whereas GPR84 recognizes medium-chain fatty acid like lauric acid. GPR120 recognizes long-chain fatty acids, especially EPA and DHA (Im, *Progress in Lipid Research,* 51:232-237(2012)). GPR120 has been detected in macrophages, dendritic cells, adipocytes, clara cells in bronchiole epithelium, and enteroendocrine L cells in colon (Miyauchi et al., *Naunyn-Schmiedebergs Arch Pharmacol.,* 379:427-434 (2009)). The antiinflammatory mechanism of omega-3 fatty acids using GPR120 knock-out mice was investigated (Oh et al., *Cell,* 142:687-698 (2010)). They suggested GPR120 activation by DHA interacts with TAB1 via b-arrestin-2, and that this interaction interrupts TAK1 activation by LPS or TNF-alpha, suppressing inflammatory responses via NF-κB and JNK in macrophages and dendritic cells (Oh et al., *Cell,* 142:687-698 (2010)). Furthermore, GPR120 activation was shown to enhance insulin-induced glucose uptake in adipose tissues through Gq/11 proteins and PI 3-kinase.

Similarly, GPR120-deficient mice fed a high-fat diet develop obesity, glucose intolerance and fatty liver with decreased adipocyte differentiation and lipogenesis and enhanced hepatic lipogenesis (Ichimura et al., *Nature,* 483 (7389):350-354 (2012). Insulin resistance in such mice was shown to be associated with reduced insulin signalling and enhanced inflammation in adipose tissue. In humans, GPR120 expression in adipose tissue was shown to be significantly higher in obese individuals than in lean controls. GPR120 gene sequencing in obese subjects revealed a deleterious non-synonymous mutation (p.R270H) that inhibits GPR120 signalling activity. Furthermore, the p.R270H variant was associated with increased risk of obesity in European populations.

Given the increase in the worldwide patient population afflicted by type 2 diabetes, there is a need for novel therapies which are effective with minimal adverse events. To decrease medical burden of type 2 diabetes through enhanced glycemic control, GPR120 modulator compounds of the present invention are being investigated here for their ability to increase glucose tolerance as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR120 modulator. Exemplary subjects include human beings of any age with risk factors for metabolic disease. Common risk factors include, but are not limited to, age, sex, weight, family history, or signs of insulin resistance such as acanthosis *nigricans*, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state. As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR120 and/or to prevent or treat the disorders listed herein. When applied to a combination, the term refers to combined amounts of the active ingredients that result in the preventive or therapeutic effect, whether administered in combination, serially, or simultaneously.

GPR120 activity was monitored by measuring phosphorylation of ERK (pERK), since G protein receptors are known to activate the ERK signaling cascade either directly and/or through recruitment of arrestin that serves as a scaffold for downstream signaling events. Molecules that activated GPR120 with sufficient potency and efficacy in the pERK assay that also possessed desirable pharmacokinetic properties were evaluated in mice for glucose lowering by monitoring disposition of an oral glucose load by an oral glucose tolerance test (oGTT).

GPR120 pERK AlphaScreen SureFire Assay

The human and mouse GPR120-mediated intracellular phosphorylated ERK assays were established using CHOAl2 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029), 500 µg/mL GENETICIN® (Life Technologies Cat. #10131-027) and 250 µg/mL Zeocin (Invitrogen Cat. #R250-01). Cells were cryo preserved at a concentration of $2\times10^7$ cells/mL, in 90% Charcoal/Dextran FBS and 10% DMSO, and frozen in liquid nitrogen at a low passage number.

For the pERK assay, $2\times10^7$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.6 \times 10^6$ cells/mL. Cells were plated into 384-well clear bottom tissue culture plates (BD Cat. #353962) at 50 µL/well, for a density of 30,000 cells/well using a MULTIDROP® and incubated for 16-18 hours (overnight) at 37° C. with 5% $CO_2$. The next day, cells were serum starved in 30 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (Labcyte Cat. #LC-0200). Cells were then stimulated with 50 nL of compound dilutions using ECHO liquid handler for 7 minutes at 37° C. Compounds ranged from final assay concentrations of 33.33 µM to 0.56 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100×(average sample–average blank)/(average total–average blank) where sample is the luminescence activity in the presence of test compound, blank is equal to the luminescence activity in the presence of DMSO control and the total is signal induced by 50 µM linolenic acid as reference compound. Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The human and mouse GPR120-mediated intracellular phosphorylated ERK assays were also established using CHO-K1 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029) and 500 µg/mL GENETICIN® (Life Technologies Cat. #10131-027). Cells were cryo preserved at a concentration of $3 \times 10^6$ cells/mL, in 70% F-12, 20% Charcoal/Dextran FBS and 10% DMSO, and frozen in liquid nitrogen at a low passage number.

For the pERK assay, $3 \times 10^6$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.5 \times 10^6$ cells/mL. Cells were plated into 384-well clear bottom tissue culture plates (BD Cat. #353962) at 50 µL/well, for a density of 25,000 cells/well using a MULTIDROP® and incubated for 16-18 hours (overnight) at 37° C. with 5% $CO_2$. The next day, cells were washed once with 50 µL of PBS without $Ca^{++}/Mg^{++}$ (Gibco Cat. #14190-036) and serum starved in 25 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (Labcyte Cat. #LC-0200). Cells were then stimulated with 40 nL of compound dilutions using ECHO liquid handler for 7 minutes at 37° C. Compounds ranged from final assay concentrations of 32 µM to 0.54 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100×(average sample–average blank)/(average total–average blank) where sample is the luminescence activity in the presence of test compound, blank is equal to the luminescence activity in the presence of DMSO control and the total is signal induced by 50 µM linolenic acid as reference compound.

Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The exemplified Examples disclosed below were tested in the GPR120 in vitro assays described above and were found having GPR120 agonist activity. Table 1 below lists the $EC_{50}$ values measured in the human GPR120 pERK assay for the following examples.

| Example Number | ($EC_{50}$ µM) |
|---|---|
| 1 | 0.61 |
| 2 | 2.47 |
| 3 | 1.11 |
| 4 | 2.74 |
| 5 | 0.43 |
| 6 | 0.40 |
| 7 | 6.91 |
| 8 | 0.27 |
| 9 | 0.28 |
| 10 | 0.68 |
| 11 | 0.87 |
| 12 | 0.54 |
| 13 | 2.69 |

-continued

| Example Number | (EC$_{50}$ µM) |
|---|---|
| 14 | 0.90 |
| 15 | 1.34 |

In Vivo GPR120 Assays

1) Acute Oral Glucose Tolerance Test

C57BL/6 mice were housed individually and fed a standard rodent chow diet. At approximately 11 weeks age, after a 5 h fast, these mice were orally treated with vehicle or test compounds 60 min before a glucose challenge (2 g/kg). Blood glucose levels were determined from tail bleeds taken at −60, 0, 15, 30, 60 and 120 min after the glucose challenge. The blood glucose excursion profile from t=0-120 min was used to calculate an area under the curve (AUC) for compound treatment. This AUC for compound treatment is compared to vehicle treatment.

2) Acute Intraperitoneal Insulin Tolerance Test

C57BL/6 mice were housed individually and fed a standard rodent chow diet. At approximately 11 weeks age, after 5 h fast, these mice were orally treated with vehicle or test compounds 30 min before an insulin challenge (0.1 U/kg). Blood glucose levels were determined from tail bleeds taken at −30, 0, 15, 30, 60, 90 and 120 min after insulin injection. The blood glucose excursion profile from t=0-120 min was used to calculate a negative area under the curve (AUC) for compound treatment. This AUC for compound treatment is compared to vehicle treatment.

The compounds of the present invention possess activity as modulators of GPR120, and, therefore, may be used in the treatment of diseases associated with GPR120 activity. Via modulation of GPR120, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, lipid disorders, lipodystrophy, liver diseases such as NASH (Non-Alcoholic SteatoHepatitis), NAFLD (Non-Alcoholic Fatty Liver Disease) and liver cirrhosis, and treatment of side-effects related to diabetes.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR120 modulators or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatitis agents, lipid lowering agents, anorectic agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin, alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, peliglitazar, tesaglitazar, aleglitazar), glucokinase activators (e.g., PF-04937319 and AMG-151, as well as other compounds described in Fyfe, M. C. T. et al., *Drugs of the Future*, 34(8):641-653 (2009) and incorporated herein by reference), GPR40 receptor modulators (e.g., TAK-875), GPR119 receptor modulators (e.g., MBX-2952, PSN821, APD597), other GPR120 receptor modulators (e.g., compound 43 from *J. Med. Chem.*, 55:4511-4515 (2012)), sodium-glucose transporter-2 (SGLT2) inhibitors (for example dapagliflozin, canagliflozin, remagliflozin), 11β-HSD-1 inhibitors (for example MK-0736, BI35585, BMS-823778, and LY2523199), amylin analogs such as pramlintide, and/or insulin. Reviews of current and emerging therapies for the treatment of diabetes can be found in: Mohler, M. L. et al., *Medicinal Research Reviews*, 29(1): 125-195 (2009), and Mizuno, C. S. et al., *Current Medicinal Chemistry*, 15:61-74 (2008).

The GPR120 receptor modulator of the present invention may also be optionally employed in combination with agents for treating complication of diabetes. These agents include PKC inhibitors and/or AGE inhibitors.

The GPR120 receptor modulator of the present invention way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 (monoacylglycerol transferase 2) inhibitors (for example, compounds from WO 2012/124744, or compound (S)-10 from *Bioorg. Med. Chem. Lett*. (2013), doi: http://dx.doi.org/10.1016/j.bmcl.2013.02.084) and the like. The compound of structure I may also be employed in combination with an agonist of the glucagon-like peptide-1 receptor (GLP-1 R), such as exenatide, liraglutide, GLP-1(1-36) amide, GLP-1 (7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery*, 5:369-370 (2006); Jones, D., *Nature Reviews: Drug Discovery*, 8:833-834 (2009); Obici, S., *Endocrinology*, 150(6):2512-2517 (2009); and Elangbam, C. S., *Vet. Pathol.*, 46(1):10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR120 receptor. Such compounds may be provided in a commercial kit, for example, for use in pharmaceutical research involving GPR120 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR120.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of multiple diseases or disorders associated with GPR120 (as defined previously). In another embodiment, the package insert states that the pharmaceutical composition can be used in combination (as defined previously) with a second therapeutic agent for the treatment of multiple diseases or disorders associated with GPR120. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples Analytical HPLC (unless otherwise noted) was performed to determine compound purity on a Shimadzu SIL-10A using the following method:

HPLC-1: SunFire C18 (4.6×150 mm) 3.5μ, gradient 10 to 100% B:A for 12 min, then 3 min hold at 100% B
  Mobile Phase A: 0.05% TFA in water:CH$_3$CN (95:5)
  Mobile Phase B: 0.05% TFA in CH$_3$CN:water (95:5)
  TFA Buffer pH=2.5
  Flow rate: 1 mL/min
  Wavelength: 254 nm, 220 nm HPLC-2: XBridge Phenyl (4.6×150 mm) 3.5μ, gradient 10 to 100% B:A for 12 min, then 3 min hold at 100% B
  Mobile Phase A: 0.05% TFA in water:CH$_3$CN (95:5)
  Mobile Phase B: 0.05% TFA in CH$_3$CN:water (95:5)
  TFA Buffer pH=2.5
  Flow rate: 1 mL/min
  Wavelength: 254 nm, 220 nm NMR Employed in Characterization of Examples NMR (nuclear magnetic resonance) spectra were typically obtained on Bruker or JEOL® 400 MHz and 500 MHz instruments in the indicated solvents. All chemical shifts are reported in ppm from tetramethylsilane with the solvent resonance as the internal standard. $^1$H NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

Spectral data are reported as chemical shift (multiplicity, number of hydrogens, coupling constants in Hz) and are reported in ppm (δ units) relative to either an internal standard (tetramethylsilane=0 ppm) for $^1$H NMR spectra, or are referenced to the residual solvent peak (2.49 ppm for CD$_3$SOCD$_2$H, 3.30 ppm for CD$_2$HOD, 1.94 for CHD$_2$CN, 7.26 ppm for CHCl$_3$, 5.32 ppm for CDHCl$_2$).

EXAMPLE 1

3-(4-((5-Chloro-2,2-dimethyl-2,3-dihydrobenzofuran-7-yl)methoxy)bicyclo[2.2.2]octan-1-yl)propanoic acid

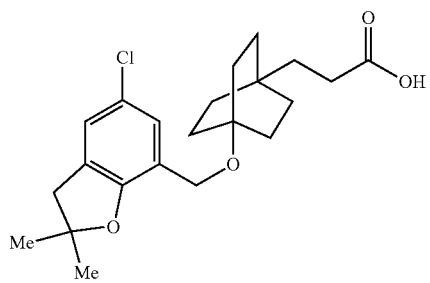 [SMILES: CC1(C)Cc2cc(Cl)cc(COC34CCC(CCC(=O)O)(CC3)CC4)c2O1]

1A. (4-Methoxybicyclo[2.2.2]octan-1-yl)methanol

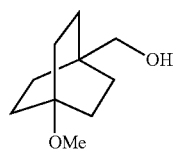 [SMILES: COC12CCC(CO)(CC1)CC2]

To a −78° C. solution of methyl 4-methoxybicyclo[2.2.2]octane-1-carboxylate (1.0 g, 5.04 mmol) in THF (20 mL) was added dropwise LiAlH$_4$ (5.04 mL of a 1 M solution in Et$_2$O, 5.04 mmol). The reaction was allowed to warm to rt and kept at rt for 30 min, then was cooled to 0° C. and quenched with EtOAc (20 mL) followed by 1 N aq. HCl (10 mL). The aqueous layer was extracted with EtOAc (3×20 mL). The combined organic extracts were washed with brine, dried over Na$_2$SO$_4$, and concentrated in vacuo to give the title compound (860 mg, 100% yield). $^1$H NMR (500 MHz, CDCl$_3$) δ 3.28 (s, 2H), 3.19 (s, 3H), 1.70-1.65 (m, 6H), 1.58-1.53 (m, 6H).

1B. 4-Methoxybicyclo[2.2.2]octane-1-carbaldehyde

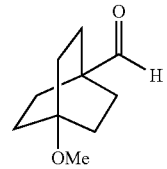 [SMILES: COC12CCC(C=O)(CC1)CC2]

To a solution of (4-methoxybicyclo[2.2.2]octan-1-yl)methanol (860 mg, 5.05 mmol) in CH$_2$Cl$_2$ (30 mL) was added Dess-Martin periodinane (2.14 g, 5.05 mmol). The reaction mixture was stirred at rt for 1 h, then was filtered through a plug of CELITE®, washed with sat'd aq. NaHCO$_3$ and brine, and dried over Na$_2$SO$_4$, and concentrated in vacuo. The crude product was purified by flash chromatography (SiO$_2$; gradient from 0 to 100% EtOAc:hexanes) to give the title compound (340 mg, 28% yield) as a white solid. LCMS, [M+H]$^+$=169.2. $^1$H NMR (500 MHz, CDCl$_3$) δ 9.43 (s, 1H), 3.16 (s, 3H), 1.77-1.72 (m, 6H), 1.71-1.64 (m, 6H).

1C. (E)-Methyl 3-(4-methoxybicyclo[2.2.2]octan-1-yl)acrylate

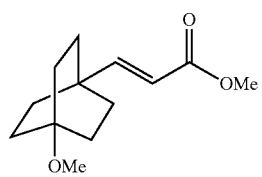 [SMILES: COC(=O)/C=C/C12CCC(OC)(CC1)CC2]

A solution of 4-methoxybicyclo[2.2.2]octane-1-carbaldehyde (340 mg, 1.42 mmol) and methyl 2-(triphenylphosphoranylidene)acetate (946 mg, 2.83 mmol) in THF (3 mL) was heated to 100° C. for 40 min in a microwave vial, then was cooled to RT and concentrated in vacuo. The crude product was chromatographed (SiO$_2$; gradient from 0 to 100% EtOAc:hexanes) to afford the title compound (230 mg, 73% yield) as a colorless oil. LCMS, [M+H]$^+$=225.2. $^1$H NMR (500 MHz, CDCl$_3$) δ 6.87 (d, J=16.0 Hz, 1H), 5.68 (d, J=16.0 Hz, 1H), 3.73 (s, 3H), 3.19 (s, 3H), 1.75-1.65 (m, 12H).

1D. Methyl 3-(4-methoxybicyclo[2.2.2]octan-1-yl)propanoate

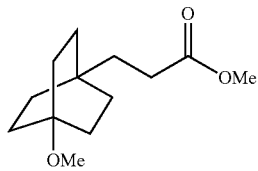 [SMILES: COC(=O)CCC12CCC(OC)(CC1)CC2]

A mixture of (E)-methyl 3-(4-methoxybicyclo[2.2.2]octan-1-yl)acrylate (230 mg, 1.03 mmol) and 10% Pd/C (55 mg, 0.051 mmol) was stirred under an atmosphere of H$_2$ at rt for 18 h. The reaction was filtered through a plug of CELITE®, and the filtrate was concentrated in vacuo to afford the title compound (230 mg, 99% yield) as a clear oil. $^1$H NMR (500 MHz, CDCl$_3$) δ 3.66 (s, 3H), 3.17 (s, 3H), 2.25-2.18 (m, 2H), 1.66-1.61 (m, 6H), 1.51-1.43 (m, 8H).

1E. Methyl 3-(4-acetoxybicyclo[2.2.2]octan-1-yl)propanoate

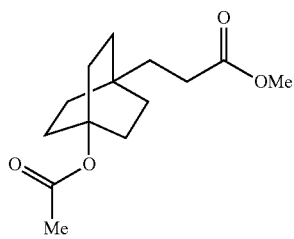 [SMILES: COC(=O)CCC12CCC(OC(C)=O)(CC1)CC2]

A mixture of methyl 3-(4-methoxybicyclo[2.2.2]octan-1-yl)propanoate (230 mg, 1.02 mmol), BF$_3$.OEt$_2$ (0.013 mL, 0.10 mmol), and Ac$_2$O (1 mL, 10.6 mmol) was stirred at rt for 60 h. The reaction mixture was poured onto ice water and extracted with Et$_2$O. The combined organic extracts were washed with sat'd aq. NaHCO$_3$, dried, and concentrated in vacuo. The crude oil was purified by flash chromatography (SiO$_2$; gradient from 0 to 10% EtOAc:hexanes) to afford the title compound (280 mg, 100% yield) as clear oil. $^1$H NMR (500 MHz, CDCl$_3$) δ 3.63 (s, 3H), 2.20-2.16 (m, 2H), 1.97-1.91 (m, 9H), 1.51-1.41 (m, 8H).

1F. 3-(4-Hydroxybicyclo[2.2.2]octan-1-yl)propanoic acid

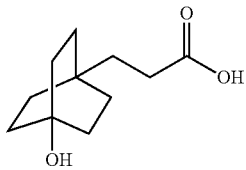 [SMILES: O=C(O)CCC12CCC(O)(CC1)CC2]

A mixture of methyl 3-(4-acetoxybicyclo[2.2.2]octan-1-yl)propanoate (280 mg, 1.101 mmol) and KOH (10% w/v in MeOH; 3.30 mmol) was stirred at rt for 3 days. Volatiles were removed in vacuo. The residue was dissolved in water, acidified to pH 2 with concentrated HCl, and then extracted with Et$_2$O (5×2 mL). The combined organic extracts were dried with MgSO$_4$ and concentrated in vacuo to give the title compound (220 mg, 100% yield) as a white solid. $^1$H NMR (500 MHz, CDCl$_3$) δ 2.30-2.21 (m, 2H), 1.64 (dd, J=10.1, 5.8 Hz, 6H), 1.55-1.44 (m, 8H).

1G. Methyl 3-(4-hydroxybicyclo[2.2.2]octan-1-yl)propanoate

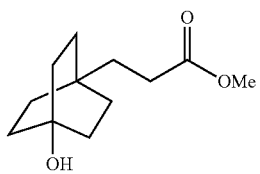 [SMILES: COC(=O)CCC12CCC(O)(CC1)CC2]

A mixture of 3-(4-hydroxybicyclo[2.2.2]octan-1-yl)propanoic acid (280 mg, 1.41 mmol) and TMSCHN$_2$ (0.71 mL, 1.41 mmol) in MeOH (1 mL) was stirred at rt for 2 h and concentrated in vacuo to afford the title compound (200 mg, 67% yield) as a clear oil. $^1$H NMR (500 MHz, CDCl$_3$) δ 2.30-2.21 (m, 2H), 1.64 (dd, J=10.1, 5.8 Hz, 6H), 1.55-1.44 (m, 8H).

1H. 2-Methylallyl 5-chloro-2-(2-methylallyloxy)benzoate

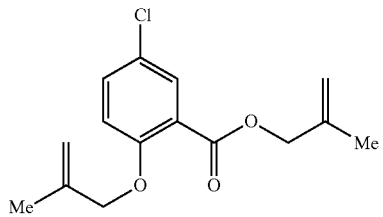 [SMILES: C=C(C)COC(=O)c1cc(Cl)ccc1OCC(=C)C]

To a solution of K$_2$CO$_3$ (20.2 g, 146 mmol) and KI (0.58 g, 3.5 mmol) in 20 mL DMF under N$_2$ was added 5-chloro-2-hydroxybenzoic acid (12 g, 69.5 mmol) in 20 ml DMF over 5 min. The reaction mixture was heated at 65° C. and 3-chloro-2-methyl-prop-1-ene (15.79 mL, 160 mmol) was added. The reaction mixture was stirred at 65° C. for 21 h, then was cooled to RT and partitioned between water and EtOAc. The organic layer was washed with H$_2$O (3×10 mL) and brine (5×10 mL), dried over MgSO$_4$, filtered, and concentrated in vacuo. The residue was purified by flash chromatography (SiO$_2$; gradient from 0 to 15% EtOAc:hexanes) to afford the title compound (20.5 g, 100% yield) as a light yellow oil. LCMS, [M+Na]$^+$=302.9. $^1$H NMR (500 MHz, CDCl$_3$) δ 7.80 (d, J=2.5 Hz, 1H), 7.39 (dd, J=8.8, 2.8 Hz, 1H), 6.90 (d, J=9.1 Hz, 1H), 5.16 (dd, J=1.5, 1.0 Hz, 1H), 5.08 (s, 1H), 5.01 (s, 1H), 5.00-4.97 (m, 1H), 4.73 (s, 2H), 4.50 (s, 2H), 1.83 (s, 6H).

1I. 2-Methylallyl 5-chloro-2-hydroxy-3-(2-methylallyl)benzoate

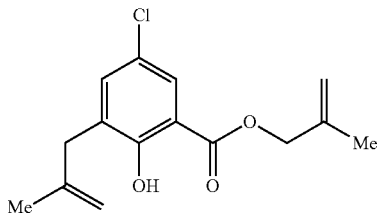 [SMILES: C=C(C)COC(=O)c1cc(Cl)cc(CC(=C)C)c1O]

2-Methylallyl 5-chloro-2-((2-methylallyl)oxy)benzoate (13.0 g, 46.3 mmol) was azeotroped several times and heated for 16 h at 195° C. to afford the title compound (13 g, 100% yield). LCMS, [M+Na]$^+$=302.9.

1J. 5-Chloro-2,2-dimethyl-2,3-dihydrobenzofuran-7-carboxylic acid

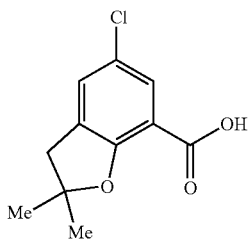 [SMILES: CC1(C)Cc2cc(Cl)cc(C(=O)O)c2O1]

A mixture of 2-methylallyl 5-chloro-2-hydroxy-3-(2-methylallyl)benzoate (7.5 g, 26.7 mmol) in formic acid (20 mL) and water (2 mL) was heated at 110° C. for 30 h. The solvent was distilled off and toluene was added and stripped off to remove the remaining formic acid. The residue was triturated with toluene to afford the title compound (3.59 g, 59% yield). LCMS, [M+H]$^+$=226.8. $^1$H NMR (500 MHz, CDCl$_3$) δ 7.84-7.80 (m, 1H), 7.33 (dt, J=2.3, 1.2 Hz, 1H), 3.10 (s, 2H), 1.60 (s, 6H).

1K. Methyl 5-chloro-2,2-dimethyl-2,3-dihydrobenzofuran-7-carboxylate

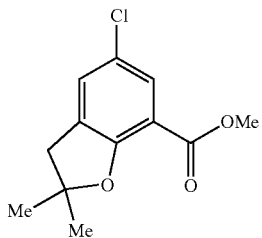 [SMILES: COC(=O)c1cc(Cl)cc2c1OC(C)(C)C2]

A mixture of 5-chloro-2,2-dimethyl-2,3-dihydrobenzofuran-7-carboxylic acid (5.0 g, 22.1 mmol) and thionyl chloride (12.9 mL, 176 mmol) in MeOH (30 mL) was heated at 60° C. for 4 h, then was cooled to RT. The reaction was concentrated in vacuo and the residue was purified by flash chromatography (SiO$_2$; gradient from 0 to 20% EtOAc:hexanes) to afford the title compound (3.36 g, 63% yield) as a white solid. LCMS, [M+H]$^+$=262.8. $^1$H NMR (500 MHz, CDCl$_3$) δ 7.71-7.67 (m, 1H), 7.24 (dt, J=2.3, 1.3 Hz, 1H), 3.89 (s, 3H), 3.00 (s, 2H), 1.54 (s, 6H).

1K. (5-Chloro-2,2-dimethyl-2,3-dihydrobenzofuran-7-yl)methanol

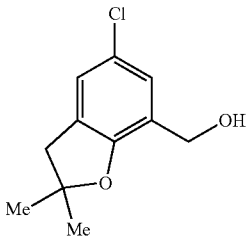 [SMILES: CC1(C)Cc2cc(Cl)cc(CO)c2O1]

To a solution of methyl 5-chloro-2,2-dimethyl-2,3-dihydrobenzofuran-7-carboxylate (5.42 g, 22.5 mmol) in THF (40 mL) at 0° C. under N$_2$ was added LAH (11.3 mL of a 2 M solution in THF, 22.5 mmol) over 15 min. The reaction was slowly warmed to RT and held at RT for 2 h. The reaction was cooled to 0° C. and quenched with EtOAc followed by 16 mL of sat'd aq. Na$_2$SO$_4$. The mixture was filtered through CELITE®. The filtrate was concentrated in vacuo. The residue was purified by flash chromatography (SiO$_2$; gradient from 0 to 40% EtOAc:hexanes) to afford the title compound (5.0 g, 93% yield). LCMS, [M–H]$^+$=211.1. $^1$H NMR (500 MHz, CDCl$_3$) δ 7.09 (s, 1H), 7.04 (s, 1H), 4.61 (d, J=6.3 Hz, 2H), 2.99 (s, 2H), 2.11 (t, J=6.2 Hz, 1H), 1.48 (s, 6H).

1L. 7-(Bromomethyl)-5-chloro-2,2-dimethyl-2,3-dihydrobenzofuran

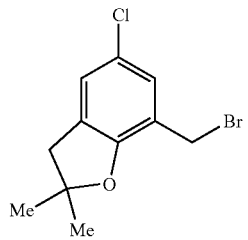 [SMILES: CC1(C)Cc2cc(Cl)cc(CBr)c2O1]

To a 0° C. mixture of (5-chloro-2,2-dimethyl-2,3-dihydrobenzofuran-7-yl)methanol (180 mg, 0.85 mmol) and NBS (181 mg, 1.02 mmol) in anhydrous DCM (5 mL) was added Ph$_3$P (266 mg, 1.02 mmol) portionwise. The reaction was then stirred at RT for 1 h, then was concentrated in vacuo. The crude residual product was purified by flash chromatography (SiO$_2$; gradient from 0 to 10% EtOAc:hexanes) to afford the title compound (190 mg, 81% yield) as a white solid. $^1$H NMR (500 MHz, CDCl$_3$) δ 7.09 (d, J=2.1 Hz, 1H), 7.02 (dt, J=2.2, 1.1 Hz, 1H), 4.40 (s, 2H), 2.98 (s, 2H), 1.48 (s, 6H).

EXAMPLE 1

A mixture of 7-(bromomethyl)-5-chloro-2,2-dimethyl-2,3-dihydrobenzofuran (26 mg, 0.094 mmol), methyl 3-(4-hydroxybicyclo[2.2.2]octan-1-yl)propanoate (10 mg, 0.047 mmol), and silver oxide (22 mg, 0.094 mmol) in EtOAc (1 mL) was stirred at 40° C. for 18 h and then at 60° C. for 3 days, then was cooled to RT. The reaction was filtered and concentrated in vacuo. The residue was purified by preparative HPLC (PHENOMENEX® Axia 5µ C18 30×100 mm column; detection at 220 nm; flow rate=40 mL/min; continuous gradient from 60% B to 100% B over 10 min+10 min hold time at 100% B, where A=90:10:0.1 H$_2$O:MeOH: TFA and B=90:10:0.1 MeOH:H$_2$O:TFA) to afford the corresponding ester (3 mg, 16% yield) as a white solid. The ester product (3 mg, 7.4 µmol) was dissolved in THF/water (1:1) (1 mL) and LiOH.H$_2$O (1 mg, 0.037 mmol) was added.

The reaction was stirred at rt for 18 h, then was acidified to pH 2 with 1 N aq. HCl and then purified by preparative HPLC (PHENOMENEX® Axia 5μ C18 30×100 mm column; detection at 220 nm; flow rate=40 mL/min; continuous gradient from 60% B to 100% B over 10 min+15 min hold time at 100% B, where A=90:10:0.1 H$_2$O:MeOH:TFA and B=90:10:0.1 MeOH:H$_2$O:TFA) to afford the title compound (3 mg, 82% yield) as a white solid. LCMS, [M−H]$^+$=391.3. $^1$H NMR (500 MHz, CDCl$_3$) δ 7.20 (dd, J=1.5, 0.6 Hz, 1H), 6.99 (s, 1H), 4.38 (s, 2H), 2.98 (s, 2H), 2.35-2.24 (m, 2H), 1.77 (dd, J=9.7, 6.1 Hz, 6H), 1.57-1.48 (m, 8H), 1.47 (s, 6H). HPLC-1: RT=12.4 min, purity=100%; HPLC-2: RT=10.7 min, purity=92.9%.

EXAMPLE 2

4-(4-((5-Chloro-2,2-dimethyl-2,3-dihydrobenzofuran-7-yl)methoxy)bicyclo[2.2.2]octan-1-yl)butanoic acid

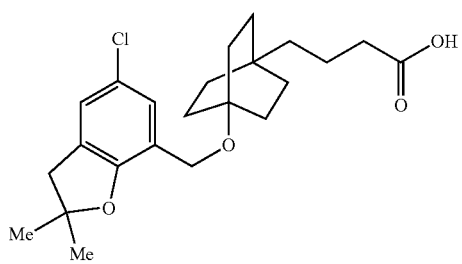 [SMILES: CC1(C)Cc2cc(Cl)cc(COC34CCC(CCCC(=O)O)(CC3)CC4)c2O1]

2A.
3-(4-Methoxybicyclo[2.2.2]octan-1-yl)propan-1-ol

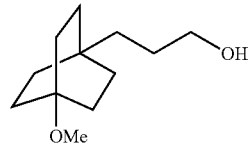 [SMILES: COC12CCC(CCCO)(CC1)CC2]

A mixture of methyl 3-(4-methoxybicyclo[2.2.2]octan-1-yl)propanoate (124 mg, 0.548 mmol) and LiBH$_4$ (0.55 mL of a 2 M solution in THF, 1.1 mmol) in THF (1 mL) was stirred at rt for 3 days, after which sat'd aq. NH$_4$Cl (0.2 mL) was added and the mixture was extracted with Et$_2$O (4×3 mL). The combined organic extracts were dried over MgSO$_4$, filtered, and concentrated in vacuo. The crude oil was purified by flash chromatography (SiO$_2$; gradient from 0 to 50% EtOAc:hexanes) to afford the title compound (99 mg, 91% yield) as clear oil. $^1$H NMR (500 MHz, CDCl$_3$) δ 3.60 (t, J=6.7 Hz, 2H), 3.19 (s, 3H), 1.71-1.59 (m, 6H), 1.57-1.41 (m, 9H), 1.19-1.10 (m, 2H).

2B.
4-(4-Methoxybicyclo[2.2.2]octan-1-yl)butanenitrile

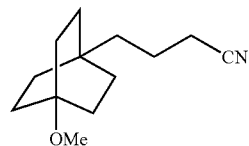

To a solution of 3-(4-methoxybicyclo[2.2.2]octan-1-yl)propan-1-ol (99 mg, 0.50 mmol) and TEA (0.167 mL, 1.20 mmol) in DCM (2 mL) was added MsCl (0.078 mL, 1.0 mmol) at 0° C. over 5 min. The reaction was stirred at rt for 2 h and concentrated in vacuo. The residue was dissolved in EtOAc (5 mL), washed with sat. aq. NaHCO$_3$ (2×5 mL), water (5 mL), and 1 N aq. HCl (5 mL). The organic layer was dried over MgSO$_4$, filtered, and concentrated in vacuo. The crude oil (~150 mg) was stirred with NaCN (98 mg, 2.0 mmol) in DMSO (2 mL) at 50° C. for 18 h. The reaction was cooled to rt and diluted with Et$_2$O (5 mL). The mixture was washed with water (5×5 mL), dried over MgSO$_4$, filtered, and concentrated in vacuo. The residue was purified by flash chromatography (SiO$_2$; gradient from 0 to 20% EtOAc:hexanes) to afford the title compound (93 mg, 90% yield) as a clear oil. $^1$H NMR (500 MHz, CDCl$_3$) δ 3.15 (s, 3H), 2.29 (t, J=7.1 Hz, 2H), 1.68-1.59 (m, 6H), 1.59-1.44 (m, 8H), 1.26-1.18 (m, 2H).

2C. 4-(3-Cyanopropyl)bicyclo[2.2.2]octan-1-yl acetate

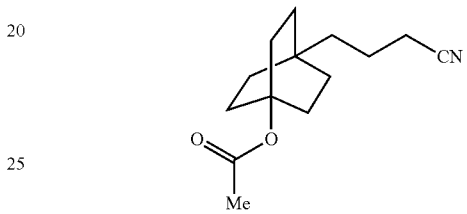

4-(3-Cyanopropyl)bicyclo[2.2.2]octan-1-yl acetate was prepared using a procedure analogous to methyl 3-(4-acetoxybicyclo[2.2.2]octan-1-yl)propanoate except that methyl 3-(4-methoxybicyclo[2.2.2]octan-1-yl)propanoate was replaced with 4-(4-methoxybicyclo[2.2.2]octan-1-yl)butanenitrile. $^1$H NMR (500 MHz, CDCl$_3$) δ 2.30 (t, J=7.1 Hz, 2H), 2.00-1.95 (m, 6H), 1.95 (s, 3H), 1.60-1.48 (m, 8H), 1.27-1.20 (m, 2H).

2D. 4-(4-Hydroxybicyclo[2.2.2]octan-1-yl)butanoic acid

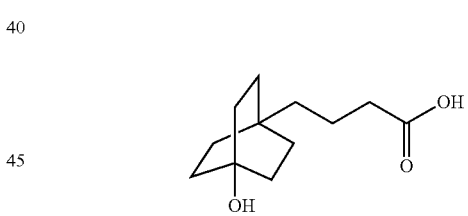

A mixture of 4-(3-cyanopropyl)bicyclo[2.2.2]octan-1-yl acetate (95 mg, 0.404 mmol), 6 N aq. KOH (1.35 mL, 8.1 mmol) in ethanol (2 mL) was stirred at 120° C. for 2 h and then cooled to RT and concentrated in vacuo. The residue was dissolved in water (5 mL) and then acidified to pH 2 with conc. HCl. The mixture was extracted with Et$_2$O (4×3 mL). The combined organic extracts were dried (MgSO$_4$) and concentrated in vacuo to afford the title compound (75 mg, 88% yield) as a white solid. $^1$H NMR (500 MHz, CDCl$_3$) δ 2.30 (t, J=7.5 Hz, 2H), 1.69-1.45 (m, 14H), 1.17-1.07 (m, 2H).

EXAMPLE 2

Example 2 was prepared using a procedure analogous to Example 1 except that 3-(4-hydroxybicyclo[2.2.2]octan-1-yl)propanoic acid was replaced with 4-(4-hydroxybicyclo[2.2.2]octan-1-yl)butanoic acid as a clear oil. LCMS, [M−H]$^+$=405.2. $^1$H NMR (500 MHz, CDCl$_3$) δ 7.20 (d, J=1.8 Hz, 1H), 6.99 (s, 1H), 4.38 (s, 2H), 2.97 (s, 2H), 2.33 (t, J=7.5 Hz, 2H), 1.80-1.71 (m, 6H), 1.63-1.50 (m, 8H), 1.47 (s, 6H), 1.20-1.10 (m, 2H). HPLC-1: RT=13.1 min, purity=100%; HPLC-2: RT=11.1 min, purity=92.7%.

EXAMPLE 3

4-(4-(3-Cyanophenoxy)bicyclo[2.2.2]octan-1-yl)butanoic acid

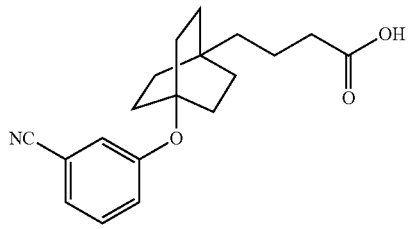 [SMILES: N#Cc1cccc(OC23CCC(CCCC(=O)O)(CC2)CC3)c1]

A mixture of 4-(4-hydroxybicyclo[2.2.2]octan-1-yl)butanoic acid (17 mg, 0.075 mmol), 3-hydroxybenzonitrile (11 mg, 0.09 mmol), Ph₃P (24 mg, 0.09 mmol), and DIAD (0.029 mL, 0.15 mmol) in toluene (1 mL) was stirred at 80° C. for 18 h. The reaction was concentrated in vacuo and purified by preparative HPLC (PHENOMENEX® Axia 5μ C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give the ester (3 mg, 12% yield) as light yellow oil. This ester (3 mg, 9.2 μmol) and 1 M aq. NaOH (0.046 mL, 0.046 mmol) in THF (0.5 mL) was stirred at rt for 18 h, then was concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to afford the title compound (2 mg, 60% yield) as a clear oil. LCMS, [M−H]⁺=312.3. ¹H NMR (500 MHz, CDCl₃) δ 7.39-7.34 (m, 2H), 7.27-7.24 (m, 1H), 7.23-7.18 (m, 1H) 2.33 (t, J=7.4 Hz, 2H), 1.88-1.78 (m, 6H), 1.62-1.49 (m, 8H), 1.21-1.11 (m, 2H). HPLC-1: RT=10.2 min, purity=93.3%; HPLC-2: RT=9.2 min, purity=95.0%.

EXAMPLE 4

3-(4-((1-(4-Chlorophenyl)-3-methyl-1H-pyrazol-5-yl)methoxy)bicyclo[2.2.2]octan-1-yl)propanoic acid

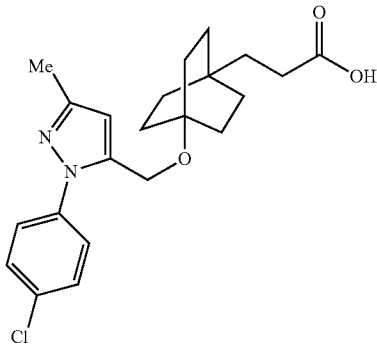 [SMILES: Cc1cc(COC23CCC(CCC(=O)O)(CC2)CC3)n(-c2ccc(Cl)cc2)n1]

4A. tert-Butyl 3-(4-hydroxybicyclo[2.2.2]octan-1-yl)propanoate

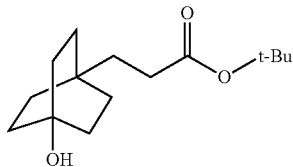 [SMILES: CC(C)(C)OC(=O)CCC12CCC(O)(CC1)CC2]

A mixture of 3-(4-hydroxybicyclo[2.2.2]octan-1-yl)propanoic acid (75 mg, 0.38 mmol) in toluene (2 mL) under an atmosphere of N₂ was heated to 80° C. 1,1-Di-tert-butoxytrimethylamine (385 mg, 1.89 mmol) was added dropwise over 3 h. The reaction mixture was heated at 80° C. for 5 h, then cooled to RT and concentrated in vacuo. The crude oil was purified by flash chromatography (SiO₂; gradient from 0 to 20% EtOAc:hexanes) to afford the title compound (89 mg, 92% yield) as a clear oil. ¹H NMR (500 MHz, CDCl₃) δ 2.15-2.09 (m, 2H), 1.66-1.60 (m, 6H), 1.54-1.47 (m, 6H), 1.47-1.39 (m, 11H).

EXAMPLE 4

A suspension of tert-butyl 3-(4-hydroxybicyclo[2.2.2]octan-1-yl)propanoate (19 mg, 0.075 mmol), 2,6-di-tert-butylpyridine (0.101 mL, 0.448 mmol), and AgOTf (115 mg, 0.45 mmol) in CH₂Cl₂ (0.5 mL) was cooled to 0° C. 5-(Bromomethyl)-1-(4-chlorophenyl)-3-methyl-1H-pyrazole (26 mg, 0.090 mmol) was added and the reaction was stirred at rt for 18 h, then was filtered. The filtrate was concentrated in vacuo and purified by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H₂O:MeOH:TFA and B=90:10:0.1 MeOH:H₂O:TFA) to give the ester as a clear oil. This ester (10 mg, 0.022 mmol) was dissolved in DCM (0.5 mL) and TFA (2 μL, 0.022 mmol) was added. The reaction was stirred at rt for 5 h. The reaction was concentrated in vacuo and purified on preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H₂O:MeOH:TFA and B=90:10:0.1 MeOH:H₂O:TFA) to afford the title compound (6.3 mg, 68% yield) as a white solid. LCMS, [M−H]⁺=401.3. ¹H NMR (500 MHz, CDCl₃) δ 7.58 (d, J=8.8 Hz, 2H), 7.43 (d, J=8.8 Hz, 2H), 6.24 (s, 1H), 4.30 (s, 2H), 2.33 (s, 3H), 2.31-2.25 (m, 2H), 1.75-1.67 (m, 6H), 1.57-1.47 (m, 8H). HPLC-1: RT=10.5 min, purity=100%; HPLC-2: RT=9.1 min, purity=95.2%.

The following Examples were prepared in a manner analogous to Example 4.

| Example No. | Name | Structure | LCMS, [M − H]+ | 1H NMR (500 MHz, CDCl3) δ | HPLC-1: RT, purity; HPLC-2: RT, purity |
|---|---|---|---|---|---|
| 5 | 3-(4-(3-Phenoxy-benzyloxy)bicyclo[2.2.2]octan-1-yl)propanoic acid | 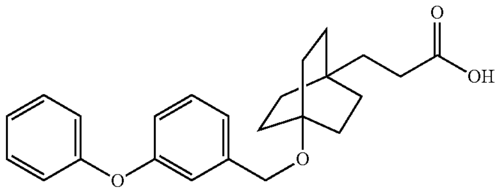 [SMILES: O=C(O)CCC12CCC(OCc3cccc(Oc4ccccc4)c3)(CC1)CC2] | 379.4 | 7.39-7.32 (m, 2H), 7.32-7.25 (m, 2H), 7.15-7.06 (m, 2H), 7.07-7.00 (m, 3H), 6.89 (dd, J = 8.0, 1.9 Hz, 1H), 4.43 (s, 2H), 2.35-2.22 (m, 2H), 1.81-1.68 (m, 7H), 1.61-1.45 (m, 9H). | 12.1 min, 95.0% 10.7 min, 90.7% |
| 6 | 3-(4-(2-Phenoxy-benzyloxy)bicyclo[2.2.2]octan-1-yl)propanoic acid | 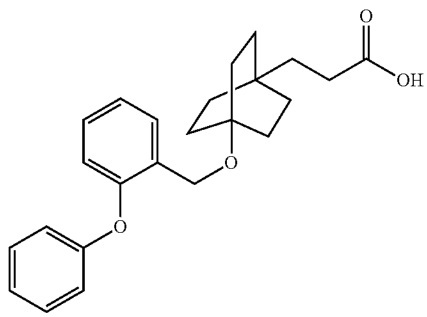 [SMILES: O=C(O)CCC12CCC(OCc3ccccc3Oc3ccccc3)(CC1)CC2] | 379.4 | 7.55 (dd, J = 7.6, 1.5 Hz, 1H), 7.38-7.30 (m, 2H), 7.23 (td, J = 7.8, 1.7 Hz, 1H), 7.15 (td, J = 7.5, 1.1 Hz, 1H), 7.12-7.06 (m, 1H), 6.99-6.93 (m, 2H), 6.88 (dd, J = 8.1, 1.0 Hz, 1H), 4.51 (s, 2H), 2.33-2.24 (m, 2H), 1.79-1.67 (m, 6H), 1.58-1.44 (m, 8H). | 12.0 min, 100% 10.2 min, 98.4% |
| 7 | 4-(4-(3-Methoxy-benzyloxy)bicyclo[2.2.2]octan-1-yl)butanoic acid | 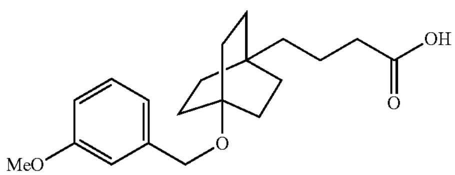 [SMILES: COc1cccc(COC23CCC(CCCC(=O)O)(CC2)CC3)c1] | 331.2 | 7.24 (t, J = 8.1 Hz, 1H), 6.95-6.89 (m, 2H), 6.82-6.78 (m, 1H), 4.44 (s, 2H), 3.83 (s, 3H), 2.33 (t, J = 7.4 Hz, 2H), 1.83-1.70 (m, 6H), 1.64-1.50 (m, 8H), 1.20-1.10 (m, 2H). | 11.0 min, 100% 9.0 min, 100% |
| 8 | 3-(4-(3-Fluoro-5-phenoxy-benzyloxy)bicyclo[2.2.2]octan-1-yl)propanoic acid | 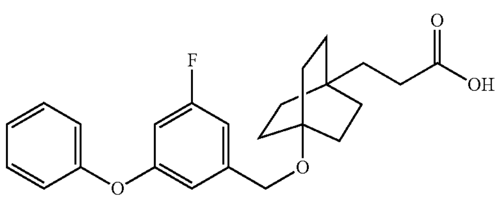 [SMILES: O=C(O)CCC12CCC(OCc3cc(F)cc(Oc4ccccc4)c3)(CC1)CC2] | 397.1 | 7.40-7.34 (m, 2H), 7.18-7.13 (m, 1H), 7.05-7.00 (m, 2H), 6.79 (dt, J = 9.4, 1.2 Hz, 1H), 6.75 (d, J = 1.4 Hz, 1H), 6.55 (dt, J = 10.0, 2.3 Hz, 1H), 4.36 (s, 2H), 2.29-2.22 (m, 2H), 1.74-1.66 (m, 6H), 1.56-1.49 (m, 6H), 1.48-1.43 (m, 2H). | 11.1 min, 100% 9.1 min, 94.2% |

EXAMPLE 9

3-(4-(5-Fluoro-2-phenoxybenzyloxy)bicyclo[2.2.2]octan-1-yl)propanoic acid

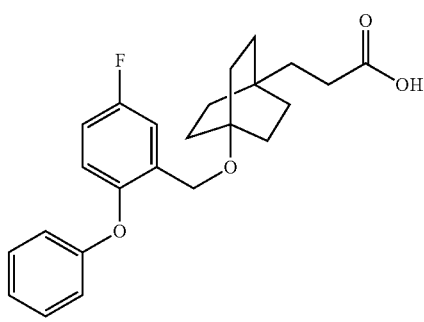 [SMILES: O=C(O)CCC12CCC(OCc3cc(F)ccc3Oc3ccccc3)(CC1)CC2]

9A. 5-Fluoro-2-phenoxybenzonitrile

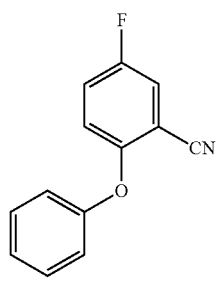 [SMILES: N#Cc1cc(F)ccc1Oc1ccccc1]

To a solution of 2,5-difluorobenzonitrile (0.5 g, 3.59 mmol) in MeCN (10 mL) was added phenol (0.507 g, 5.4 mmol) and K2CO3 (0.50 g, 3.6 mmol). The mixture was stirred for 3 h at 100° C., then cooled to rt. The solution was diluted with EtOAc and washed with sat'd aq. NaHCO3 and 10% aq. LiCl. The organic layer was dried (MgSO4) and concentrated in vacuo. The residue was purified by flash chromatography (SiO$_2$; gradient from 10% EtOAc:hexanes) to afford the title compound (0.65 g, 81% yield). $^1$H NMR (500 MHz, CDCl$_3$) δ 7.41 (dd, J=8.7, 7.6 Hz, 2H), 7.37 (dd, J=7.4, 3.0 Hz, 1H), 7.25-7.19 (m, 2H), 7.09-7.04 (m, 2H), 6.89 (dd, J=9.2, 4.3 Hz, 1H).

9B. 5-Fluoro-2-phenoxybenzaldehyde

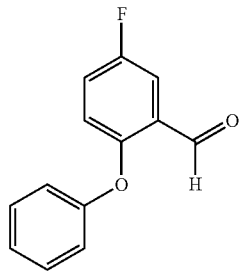 [SMILES: O=Cc1cc(F)ccc1Oc1ccccc1]

To a solution of 5-fluoro-2-phenoxybenzonitrile (0.7 g, 3.28 mmol) in 10 mL DCM was added DIBAL-H (3.28 mL of a 1 M solution in DCM; 3.28 mmol) at −78° C. The solution was stirred for 2 h at −78° C. and 10 mL of 1 N aq. HCl was added. The mixture was warmed to rt and stirred for 1 h. The organic layer was separated. The aqueous layer was extracted with DCM. The combined organic extracts were dried (MgSO$_4$) and concentrated in vacuo. The residue was purified by flash chromatography (SiO$_2$; 10% EtOAc: hexanes) to afford the title compound (0.60 g, 80% yield). $^1$H NMR (500 MHz, CDCl$_3$) δ 10.44 (d, J=3.0 Hz, 1H), 7.63-7.60 (m, 1H), 7.42-7.37 (m, 2H), 7.27-7.22 (m, 1H), 7.21-7.17 (m, 1H), 7.06-7.02 (m, 2H), 6.94 (dd, J=9.1, 4.1 Hz, 1H).

9C. (5-Fluoro-2-phenoxyphenyl)methanol

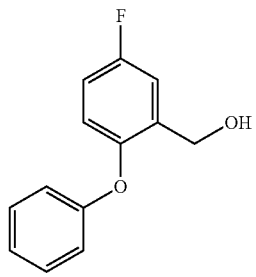 [SMILES: OCc1cc(F)ccc1Oc1ccccc1]

To a solution of 5-fluoro-2-phenoxybenzaldehyde (0.60 g, 2.8 mmol) in MeOH (10 mL) was added NaBH$_4$ (0.136 g, 3.6 mmol) at 0° C. and the reaction was stirred at rt for 1 h. The reaction was quenched with sat'd aq. NaHCO$_3$ and concentrated in vacuo. The residue was taken up with EtOAc and washed with sat'd aq. NaHCO$_3$. The organic layer was dried (MgSO$_4$) and concentrated in vacuo to give the title compound (0.53 g, 83% yield). $^1$H NMR (500 MHz, CDCl$_3$) δ 7.35-7.31 (m, 2H), 7.24 (dd, J=8.8, 3.0 Hz, 1H), 7.12-7.07 (m, 1H), 6.96-6.92 (m, 2H), 6.90-6.82 (m, 2H), 4.72 (s, 2H).

9D. 2-(Bromomethyl)-4-fluoro-1-phenoxybenzene

To a 0° C. solution of (5-fluoro-2-phenoxyphenyl)methanol (0.35 g, 1.6 mmol) in DCM (5 mL) was added PBr$_3$ (1.76 mL of a 1 M solution in DCM; 1.76 mmol). The solution was stirred at 0° C. for 1 h. Sat'd aq. NaHCO$_3$ was added and the mixture was warmed to rt and extracted with DCM. The organic layer was dried (MgSO$_4$) and concentrated in vacuo. The residue was purified by flash chromatography (SiO$_2$; 10% EtOAc:hexanes) to afford the title compound (0.06 g, 12% yield). $^1$H NMR (500 MHz, CDCl$_3$) δ 7.32-7.27 (m, 2H), 7.17 (dd, J=9.1, 3.0 Hz, 1H), 7.08-7.02 (m, 1H), 6.94-6.89 (m, 1H), 6.89-6.84 (m, 3H), 3.77 (s, 2H).

EXAMPLE 9

Example 9 was prepared using a procedure analogous to Example 4 except that 5-(bromomethyl)-1-(4-chlorophenyl)-3-methyl-1H-pyrazole was replaced with 2-(bromomethyl)-4-fluoro-1-phenoxybenzene. LCMS, [M−H]$^+$=397.1. $^1$H NMR (500 MHz, CD$_2$Cl$_2$) δ 7.21 (dd, J=8.80, 7.43 Hz, 2H), 7.17 (dd, J=9.35, 3.03 Hz, 1H), 6.94-7.00 (m, 1H), 6.81-6.85 (m, 1H), 6.78-6.81 (m, 2H), 6.73-6.77 (m, 1H), 4.32 (s, 2H), 2.12-2.18 (m, 2H), 1.54-1.60 (m, 6H), 1.37-1.42 (m, 6H), 1.32-1.37 (m, 2H). HPLC-1: RT=11.0 min, purity=100%; HPLC-2: RT=9.0 min, purity=94.0%.

EXAMPLE 10

2-((4-(3-Phenoxybenzyloxy)bicyclo[2.2.2]octan-1-yl)methoxy)acetic acid

10A. Methyl 4-(3,5-difluorobenzoyl)bicyclo[2.2.2]octane-1-carboxylate

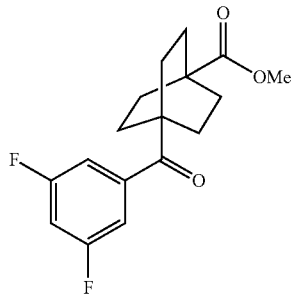 [SMILES: COC(=O)C12CCC(C(=O)c3cc(F)cc(F)c3)(CC1)CC2]

To a mixture of dimethyl bicyclo[2.2.2]octane-1,4-dicarboxylate (2.0 g, 8.84 mmol) in 10 mL MeOH was added NaOH (0.35 g, 8.8 mmol) and 0.5 mL water. The mixture was stirred at 75° C. for 4 h and at rt for 12 h. The mixture was diluted with water and washed with Et$_2$O. The aqueous layer was acidified to pH 2 with 1 N aq. HCl and filtered. The filtrate was extracted with CHCl$_3$. The extract was dried and concentrated in vacuo to give 4-(methoxycarbonyl)bicyclo[2.2.2]octane-1-carboxylic acid (1.2 g, 58% yield). To the above acid (1.2 g, 5.65 mmol) was added SOCl$_2$ (10 mL, 5.65 mmol). The mixture was stirred for at 90° C. for 3 h. The solution was concentrated in vacuo and re-dissolved in DCM and concentrated in vacuo 3 times to remove excess SOCl$_2$. The residue (1.0 g, 4.3 mmol) was dissolved in 10 mL THF and acetylacetone iron (III) salt (0.046 g, 0.13 mmol) was added. The orange mixture was cooled to 0° C. and (3,5-difluorophenyl)magnesium bromide (11.3 mL of a 0.5 M solution in THF, 5.64 mmol) was added dropwise. The mixture was stirred at 0° C. for 2 h. 1 N aq. HCl was added and the mixture was extracted with EtOAc. The combined organic layers were dried (MgSO$_4$) and concentrated in vacuo. The residue was purified by flash chromatography (SiO$_2$; 10% EtOAc: hexanes) to afford the title compound (0.9 g, 67% yield). $^1$H NMR (500 MHz, CDCl$_3$) δ 7.06-7.12 (m, 2H), 6.93 (tt, J=8.63, 2.24 Hz, 1H), 3.69 (s, 3H), 1.93-1.98 (m, 6H), 1.88-1.93 (m, 6H).

10B. 4-(3,5-Difluorobenzoyloxy)bicyclo[2.2.2]octane-1-carboxylic acid

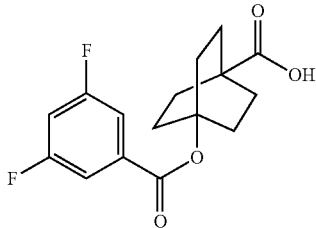 [SMILES: O=C(OC12CCC(C(=O)O)(CC1)CC2)c1cc(F)cc(F)c1]

To a solution of methyl 4-(3,5-difluorobenzoyl)bicyclo[2.2.2]octane-1-carboxylate (0.5 g, 1.62 mmol) in 10 mL MeOH was added NaOH (0.130 g, 3.24 mmol) and 1 mL of water. The mixture was stirred for at 75° C. for 3 h, then cooled to RT and concentrated in vacuo. The residue was dissolved in 20 mL of water and acidified to pH 2 with 1 N aq. HCl. The white precipitate was filtered and dried to afford 4-(3,5-difluorobenzoyl)bicyclo[2.2.2]octane-1-carboxylic acid (0.42 g, 84% yield). To the above acid (0.42 g, 1.36 mmol) in 5 mL of TFA was added 30% H$_2$O$_2$ (0.56 mL, 5.4 mmol) and the solution was stirred at 50° C. for 4 h. The mixture was cooled to 0° C. and sodium metabisulfite (0.258 g, 1.36 mmol) in 5 mL of water was added. The mixture was stirred for 2 h at 0° C. The precipitate was filtered and washed with water and dried to afford the title compound (0.395 g, 89% yield). $^1$H NMR (500 MHz, CD$_2$Cl$_2$) δ 7.33-7.43 (m, 2H), 6.87-6.96 (m, 1H), 2.06-2.16 (m, 6H), 1.92-2.02 (m, 6H).

10C. 4-(Hydroxymethyl)bicyclo[2.2.2]octan-1-yl 3,5-difluorobenzoate

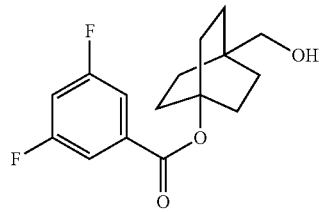 [SMILES: O=C(OC12CCC(CO)(CC1)CC2)c1cc(F)cc(F)c1]

To a solution of 4-((3,5-difluorobenzoyl)oxy)bicyclo[2.2.2]octane-1-carboxylic acid (0.336 g, 1.083 mmol) in 10 mL THF was added BH$_3$.THF (1.08 mL of a 1M solution in THF, 1.08 mmol) at 0° C. The solution was stirred at rt for 2 h and sat'd aq. NaHCO$_3$ was added. The mixture was extracted with EtOAc. The organic layer was dried and concentrated in vacuo. The residue was purified by flash chromatography (SiO$_2$; 20% EtOAc: hexanes) to afford the title compound (0.16 g, 47% yield). $^1$H NMR (500 MHz, CD$_2$Cl$_2$) δ 7.52-7.43 (m, 2H), 7.04-6.97 (m, 1H), 3.22 (s, 2H), 2.15-2.09 (m, 6H), 1.65-1.58 (m, 6H).

10D. 4-((2-tert-Butoxy-2-oxoethoxy)methyl)bicyclo[2.2.2]octan-1-yl 3,5-difluorobenzoate

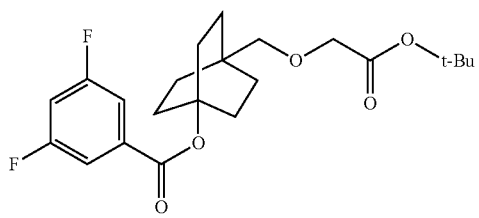 [SMILES: CC(C)(C)OC(=O)COCC12CCC(OC(=O)c3cc(F)cc(F)c3)(CC1)CC2]

To a solution of 4-(hydroxymethyl)bicyclo[2.2.2]octan-1-yl 3,5-difluorobenzoate (50 mg, 0.17 mmol) in 5 mL toluene was added tert-butyl 2-bromoacetate (49 mg, 0.25 mmol), Bu$_4$NCl (15 mg, 0.051 mmol), and 30% aq. NaOH (5 mL, 0.169 mmol). The mixture was stirred at rt for 4 days. The mixture was taken up with EtOAc and washed with 1 N aq. HCl. The organic layer was dried (MgSO$_4$) and concentrated in vacuo. The residue was purified by preparative HPLC (PHENOMENEX® Axia 5μ C18 30×100 mm column; detection at 220 nm; flow rate=40 mL/min; continuous gradient from 70% B to 100% B over 10 min+5 min hold time at 100% B, where A=90:10:0.1 H$_2$O:MeOH:TFA and B=90:10:0.1 MeOH:H₂O:TFA) to afford the title compound (40 mg, 56% yield). $^1$H NMR (500 MHz, CD₂Cl₂) δ 7.48 (dd, J=7.8, 2.3 Hz, 2H), 7.00 (tt, J=8.7, 2.4 Hz, 1H), 3.89 (s, 2H), 3.14 (s, 2H), 2.10 (s, 6H), 1.70-1.64 (m, 6H), 1.46 (s, 9H).

EXAMPLE 10

To a solution of 4-((2-(tert-butoxy)-2-oxoethoxy)methyl)bicyclo[2.2.2]octan-1-yl 3,5-difluorobenzoate (30 mg, 0.073 mmol) in 5 mL THF was added LiOH.H₂O (3.5 mg, 0.15 mmol) and 1 mL of water. The mixture was stirred at rt for 6.5 h, then acidified with 1 N aq. HCl. The mixture was concentrated in vacuo. The residue was taken up in EtOAc and washed with 1 N aq. HCl. The organic layer was dried (MgSO₄) and concentrated in vacuo to give a mixture of tert-butyl 2-((4-hydroxybicyclo[2.2.2]octan-1-yl)methoxy)acetate and 2-((4-hydroxybicyclo[2.2.2]octan-1-yl)methoxy)acetic acid. The mixture was taken up in 5 mL of DCM and 1-(chloromethyl)-3-phenoxybenzene (56 mg, 0.26 mmol) was added, followed by 2,6-di-tert-butylpyridine (49 mg, 0.26 mmol). The mixture was stirred for at rt for 5 min and AgOTf (60 mg, 0.23 mmol) was added. The reaction was stirred at rt for 18 h, then was taken up in DCM and washed with sat'd aq. NaHCO₃. The organic layer was dried (MgSO₄) and concentrated in vacuo. The residue was dissolved in 5 mL MeOH and 2 mL 1 N aq. NaOH was added. The mixture was stirred at rt for 6 h and neutralized with 1 N aq. HCl. The mixture was concentrated in vacuo. The residue was taken up in EtOAc and washed with 1 N aq. HCl. The organic layer was dried (MgSO₄) and concentrated in vacuo. The residue was purified by preparative HPLC (PHENOMENEX® Axia 5µ C18 30×100 mm column; detection at 220 nm; flow rate=40 mL/min; continuous gradient from 30% B to 100% B over 10 min+5 min hold time at 100% B, where A=90:10:0.1 H₂O:ACN:TFA and B=90:10:0.1 ACN:H₂O:TFA) to afford the title compound (6 mg, 20% yield) as a white solid. LCMS, [M−H]⁺=395.4. $^1$H NMR (500 MHz, CD₂Cl₂) δ 7.21-7.27 (m, 2H), 7.18 (t, J=7.98 Hz, 1H), 6.99-7.03 (m, 1H), 6.96 (d, J=7.70 Hz, 1H), 6.87-6.92 (m, 3H), 6.77 (dd, J=8.25, 1.93 Hz, 1H), 4.30 (s, 2H), 3.95 (s, 2H), 3.12 (s, 2H), 1.61-1.68 (m, 6H), 1.48-1.54 (m, 6H). HPLC-1: RT=10.5 min, purity=100%; HPLC-2: RT=8.7 min, purity=95.0%.

EXAMPLE 11

3-(4-(3-Fluoro-5-isopropoxybenzyloxy)bicyclo[2.2.2]octan-1-yl)propanoic acid

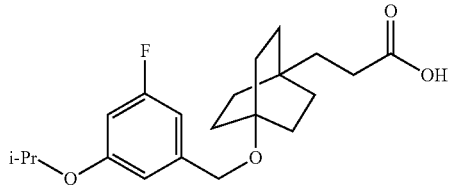 [SMILES: CC(C)Oc1cc(F)cc(COC23CCC(CCC(=O)O)(CC2)CC3)c1]

11A. (E)-4-(3-Methoxy-3-oxoprop-1-enyl)bicyclo[2.2.2]octan-1-yl 3,5-difluorobenzoate

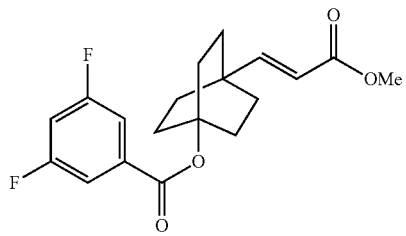 [SMILES: COC(=O)/C=C/C12CCC(OC(=O)c3cc(F)cc(F)c3)(CC1)CC2]

(E)-4-(3-Methoxy-3-oxoprop-1-enyl)bicyclo[2.2.2]octan-1-yl 3,5-difluorobenzoate was prepared using a procedure analogous to (E)-methyl 3-(4-methoxybicyclo[2.2.2]octan-1-yl)acrylate except that (4-methoxybicyclo[2.2.2]octan-1-yl)methanol was replaced with 4-(hydroxymethyl)bicyclo[2.2.2]octan-1-yl 3,5-difluorobenzoate. $^1$H NMR (500 MHz, CDCl₃) δ7.49 (dd, J=7.70, 2.20 Hz, 2H), 6.96-7.05 (m, 1H), 6.89 (d, J=15.96 Hz, 1H), 5.73 (d, J=15.96 Hz, 1H), 3.76 (s, 3H), 2.13-2.25 (m, 6H), 1.73-1.83 (m, 6H).

11B. (E)-Methyl 3-(4-hydroxybicyclo[2.2.2]octan-1-yl)acrylate

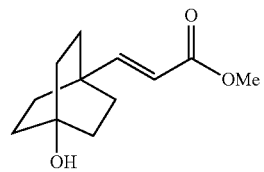 [SMILES: COC(=O)/C=C/C12CCC(O)(CC1)CC2]

To a solution of (E)-4-(3-methoxy-3-oxoprop-1-en-1-yl)bicyclo[2.2.2]octan-1-yl 3,5-difluorobenzoate (0.17 g, 0.485 mmol) in 10 mL of methanol was added NaOMe (0.210 g, 0.970 mmol). The solution was stirred at rt for 3 h. The solution was acidified to pH 2 with 1 N aq. HCl and concentrated in vacuo. The residue was taken up with EtOAc and washed with 1 N aq. HCl. The organic layer was dried (MgSO₄) and concentrated in vacuo to give the title compound (0.105 g, 93% yield) as a white solid. $^1$H NMR (500 MHz, CDCl₃) δ 6.86 (d, J=16.0 Hz, 1H), 5.68 (d, J=16.0 Hz, 1H), 3.73 (s, 3H), 1.70 (s, 12H).

11C. Methyl 3-(4-hydroxybicyclo[2.2.2]octan-1-yl)propanoate

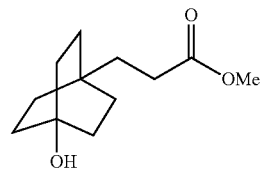 [SMILES: COC(=O)CCC12CCC(O)(CC1)CC2]

Methyl 3-(4-hydroxybicyclo[2.2.2]octan-1-yl)propanoate was prepared using a procedure analogous to methyl 3-(4-methoxybicyclo[2.2.2]octan-1-yl)propanoate except that (E)-methyl 3-(4-methoxybicyclo[2.2.2]octan-1-yl)acrylate was replaced with (E)-methyl 3-(4-hydroxybicyclo[2.2.2]octan-1-yl)acrylate. $^1$H NMR (500 MHz, CDCl$_3$) δ 3.66 (s, 3H), 2.30-2.21 (m, 2H), 1.64 (dd, J=10.1, 5.8 Hz, 6H), 1.55-1.44 (m, 8H).

Example 11

Example 11 was prepared using a procedure analogous to Example 4 except that tert-butyl 3-(4-hydroxybicyclo[2.2.2]octan-1-yl)propanoate was replaced with methyl 3-(4-hydroxybicyclo[2.2.2]octan-1-yl)propanoate (10 mg, 16.3% yield) as a white lyophilate. LCMS, [M−H]$^+$=363.0. $^1$H NMR (500 MHz, CD$_2$Cl$_2$) δ 6.53 (s, 1H) 6.51 (d, J=9.35 Hz, 1H), 6.38 (dt, J=10.94, 2.24 Hz, 1H), 4.42 (dt, J=12.10, 6.05 Hz, 1H), 4.26 (s, 2H), 2.15-2.20 (m, 2H), 1.60-1.66 (m, 6H), 1.42-1.47 (m, 6H), 1.35-1.41 (m, 2H), 1.22 (d, J=6.05 Hz, 6H). HPLC-1: RT=13.9 min, purity=100%; HPLC-2: RT=12.2 min, purity=100%.

EXAMPLE 12

3-(4-(3-Fluoro-5-(4-fluorophenoxy)benzyloxy)bicyclo[2.2.2]octan-1-yl)propanoic acid

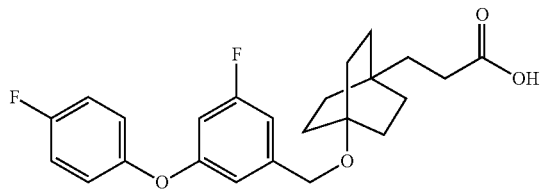 [SMILES: O=C(O)CCC12CCC(OCc3cc(F)cc(Oc4ccc(F)cc4)c3)(CC1)CC2]

Example 12 (10 mgs, 14% yield; white lyophilate) was prepared using a procedure analogous to Example 11 except that 1-(bromomethyl)-3-fluoro-5-isopropoxybenzene was replaced with 1-(bromomethyl)-3-fluoro-5-(4-fluorophenoxy)benzene. LCMS, [M−H]$^+$=415.1. $^1$H NMR (500 MHz, CD$_2$Cl$_2$) δ 6.96-7.01 (m, 2H), 6.89-6.94 (m, 2H), 6.69 (dd, J=9.22, 0.96 Hz, 1H), 6.62 (s, 1H), 6.42 (dt, J=10.18, 2.34 Hz, 1H), 4.27 (s, 2H), 2.15-2.19 (m, 2H), 1.57-1.63 (m, 6H), 1.40-1.46 (m, 6H), 1.35-1.39 (m, 2H). HPLC-1: RT=13.9 min, purity=100%; HPLC-2: RT=12.2 min, purity=100%.

EXAMPLE 13

(E)-3-(4-(((5-Chloro-2,2-dimethyl-2,3-dihydrobenzofuran-7-yl)oxy)methyl)bicyclo[2.2.2]octan-1-yl)acrylic acid

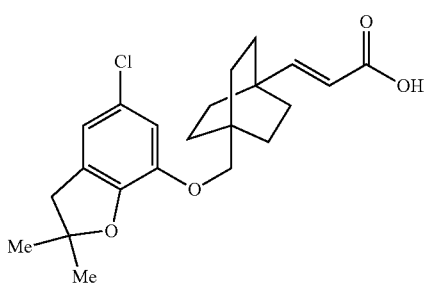 [SMILES: CC1(C)Cc2cc(Cl)cc(OCC34CCC(/C=C/C(=O)O)(CC3)CC4)c2O1]

13A. 2,2-Dimethyl-2,3-dihydrobenzofuran-7-yl acetate

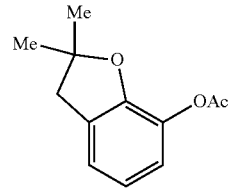 [SMILES: CC(=O)Oc1cccc2c1OC(C)(C)C2]

To a solution of 2,2-dimethyl-2,3-dihydrobenzofuran-7-ol (5 g, 30.5 mmol) in CH$_2$Cl$_2$ (25 mL) was added acetic anhydride (3.73 g, 36.5 mmol), followed by pyridine (2.46 mL, 30.5 mmol), the reaction mixture was stirred at RT for 18 h. Water (10 mL) was added to the reaction mixture; the organic layer was washed with brine, dried over MgSO$_4$, filtered and concentrated in vacuo to afford the title compound (8.1 g, 97% yield; 75% purity by LC/MS) as a colorless oil. LCMS, [M+H]$^+$=407, $^1$H NMR (400 MHz, CDCl$_3$) δ 7.07-6.94 (m, 1H), 6.88-6.83 (m, 1H), 6.82-6.76 (m, 1H), 3.04 (s, 2H), 2.31 (s, 3H), 1.48 (s, 6H)

13B. 5-Chloro-2,2-dimethyl-2,3-dihydrobenzofuran-7-yl acetate

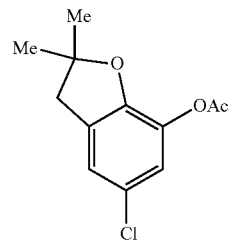 [SMILES: CC(=O)Oc1cc(Cl)cc2c1OC(C)(C)C2]

To a solution of 2,2-dimethyl-2,3-dihydrobenzofuran-7-yl acetate (8.1 g, 29.5 mmol) in acetic acid (60 mL) was added N-chlorosuccinimide (6.5 g, 48.7 mmol). The reaction mixture was heated to 60° C. for 5 h. The reaction was cooled down to room temperature. The mixture was concentrated in vacuo to reduce the volume to about 1/3. Water (12.5 mL) was added in and the mixture was cooled to 0° C. A NaOH solution (20%) was slowly added in to adjust pH to about 7. The solution was extract twice with Et$_2$O. The combined organic fraction was washed with water, brine, dried over MgSO$_4$, filtered and concentrated in vacuo to afford the crude. The crude oil was purified by flash chromatography (SiO$_2$; gradient from 20 to 50% EtOAc:hexanes) to afford the title compound (6.74 g, 95% yield; 99% pure by LC/MS) as white solid. LCMS, [M+H]$^+$=441.

13C. 5-Chloro-2,2-dimethyl-2,3-dihydrobenzofuran-7-ol

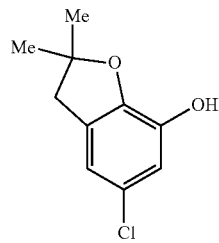

To a solution of 5-chloro-2,2-dimethyl-2,3-dihydrobenzofuran-7-yl acetate (6.74 g, 28 mmol) in MeOH (25 mL) was added a 20% of NaOH (30 mL) solution at 0° C. The reaction mixture was stirred at 12° C.~18° C. for 30 min, concentrated in vacuo and cooled to 0° C. The pH of the solution was adjusted to ~3 with 10% HCl. The solid was filtered and washed three times with cold water and dried under vacuo to afford title compound (5.5 g, 99% yield, 99% pure by LC/MS) as a light yellow solid. LCMS, $[M+H]^+$=199.

13D. Methyl 4-(((5-chloro-2,2-dimethyl-2,3-dihydrobenzofuran-7-yl)oxy)methyl)bicyclo[2.2.2]octane-1-carboxylate

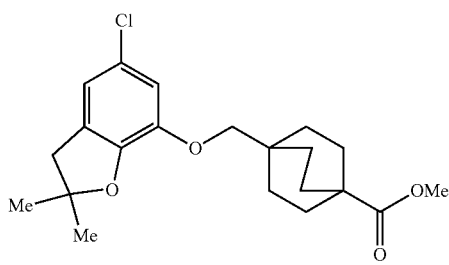 [SMILES: COC(=O)C12CCC(COc3cc(Cl)cc4c3OC(C)(C)C4)(CC1)CC2]

To a solution of 5-chloro-2,2-dimethyl-2,3-dihydrobenzofuran-7-ol (108 mg, 0.545 mmol), methyl 4-(hydroxymethyl)bicyclo[2.2.2]octane-1-carboxylate (90 mg, 0.454 mmol) and triphenylphosphine (179 mg, 0.681 mmol) in toluene (2 mL) at 0° C. was added (E)-di-tert-butyl diazene-1,2-dicarboxylate (157 mg, 0.681 mmol) in toluene (0.5 mL) slowly. The reaction mixture was stirred at room temperature for 5 min and the reaction mixture was heated to 90° C. for 18 hours. After cooled to room temperature, dichloromethane (5 mL) and water (5 mL) were added to the reaction mixture. The layers were separated. The organic layer was washed with brine, dried over MgSO₄, filtered and concentrated in vacuo to afford the crude. This crude was purified by preparative HPLC (PHENOMENEX® Axia 5 μm C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give the title compound (75 mg, 41.5% Yield; 95% pure by LC/MS) as a light yellow oil. $[M+Na]^+$=401, ¹H NMR (400 MHz, CDCl₃) δ 6.70 (dd, J=14.3, 1.6 Hz, 2H), 3.65 (s, 3H), 3.63 (s, 2H), 2.96 (s, 2H), 1.86-1.77 (m, 6H), 1.59-1.55 (m, 6H), 1.48 (s, 6H).

13E. (4-(((5-Chloro-2,2-dimethyl-2,3-dihydrobenzofuran-7-yl)oxy)methyl)bicyclo[2.2.2]octan-1-yl)methanol

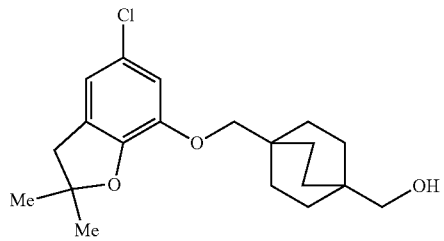 [SMILES: CC1(C)Cc2cc(Cl)cc(OCC34CCC(CO)(CC3)CC4)c2O1]

To a solution of methyl 4-(((5-chloro-2,2-dimethyl-2,3-dihydrobenzofuran-7-yl)oxy)methyl)bicyclo[2.2.2]octane-1-carboxylate (70.0 mg, 0.185 mmol) in THF (0.4 mL) at 0° C. was added LAH (0.092 mL, 2N in CH₂Cl₂, 0.185 mmol) dropwise. The reaction mixture was held at 0° C. for 30 min, then warmed to rt and stirred at room temperature for 1 hour. The reaction was cooled to 0° C., and quenched by the addition of EtOAc and saturated Na₂SO₄ (0.2 mL) aqueous solution., The mixture was filtered and the filtrate was concentrated in vacuo to give the title compound (70 mg, 100% yield, 93% pure by LC/MS) as a white solid $[M+Na]^+$=373, ¹H NMR (400 MHz, CDCl₃) δ 6.78-6.64 (m, 2H), 3.62 (s, 2H), 3.29 (d, J=5.8 Hz, 2H), 2.95 (s, 2H), 1.60-1.55 (m, 6H), 1.47 (s, 6H), 1.50-1.41 (m, 6H).

13F. 4-(((5-Chloro-2,2-dimethyl-2,3-dihydrobenzofuran-7-yl)oxy)methyl)bicyclo[2.2.2]octane-1-carbaldehyde

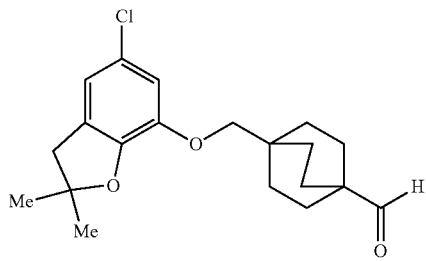 [SMILES: CC1(C)Cc2cc(Cl)cc(OCC34CCC(C=O)(CC3)CC4)c2O1]

To a solution of (4-(((5-chloro-2,2-dimethyl-2,3-dihydrobenzofuran-7-yl)oxy)methyl)bicyclo[2.2.2]octan-1-yl)methanol (65 mg, 0.185 mmol) in dichloromethane (1 mL) was added Dess-Martin periodinane (79 mg, 0.185 mmol). The mixture was stirred at room temperature for 1 hour. A saturated aqueous solution of NaHCO₃—Na₂S₂O₃ (1 mL, 1:1) and dichloromethane (5 mL) was added in. The mixture was stirred at room temperature for 5 min. The organic layer was separated, washed with brine, dried over MgSO₄, filtered and concentrated in vacuo to afford the crude. The crude product was purified by flash chromatography (SiO₂; gradient from 0 to 40% EtOAc:hexanes) to afford the title compound (48 mg, 74% yield) as white solid. ¹H NMR (400 MHz, CDCl₃) δ 9.47 (s, 1H), 6.74-6.72 (m, 1H), 6.69 (d, J=2.0 Hz, 1H), 3.65 (s, 2H), 2.96 (s, 2H), 1.73-1.57 (m, 12H), 1.47 (s, 6H).

13G. (E)-Ethyl 3-(4-(((5-Chloro-2,2-dimethyl-2,3-dihydrobenzofuran-7-yl)oxy)methyl)bicyclo[2.2.2]octan-1-yl)acrylate

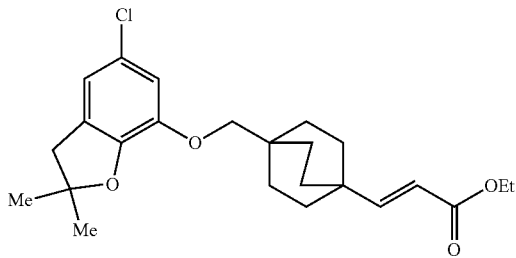 [SMILES: CCOC(=O)/C=C/C12CCC(COc3cc(Cl)cc4c3OC(C)(C)C4)(CC1)CC2]

A solution of 4#(5-chloro-2,2-dimethyl-2,3-dihydrobenzofuran-7-yl)oxy)methyl)bicyclo[2.2.2]octane-1-carbaldehyde (47 mg, 0.135 mmol) and methyl 2-(triphenylphosphoranylidene)acetate (67.6 mg, 0.202 mmol) in THF (1 mL) was heated to 100° C. for 18 h. After cooled to room temperature, the reaction was diluted with EtOAc, washed with brine, dried over MgSO₄, filtered and concentrated in vacuo to afford the crude. This crude was purified by preparative HPLC (PHENOMENEX® Axia 5 μm C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give title compound (26.5 mg, 54.6% yield, 99% pure by LC/MS) as a colorless oil. [M+H]⁺=419, ¹H NMR (400 MHz, CDCl₃) δ 6.88 (d, J=15.9 Hz, 1H), 6.70 (dd, J=11.4, 1.5 Hz, 2H), 5.67 (d, J=15.9 Hz, 1H), 4.19 (q, J=7.1 Hz, 2H), 3.63 (s, 2H), 2.96 (s, 2H), 1.59 (s, 12H), 1.47 (s, 6H), 1.29 (t, J=7.2 Hz, 3H).

EXAMPLE 13

To a solution of (E)-ethyl 3-(4-(((5-chloro-2,2-dimethyl-2,3-dihydrobenzofuran-7-yl)oxy)methyl)bicyclo[2.2.2]octan-1-yl)acrylate (26 mg, 0.062 mmol) in THF (1 mL) was added LiOH.H₂O (13 mg, 0.31 mmol) in water (0.5 mL). The reaction mixture was stirred overnight, after which 1 N aq. NaOH (0.3 mL) and MeOH (0.1 mL) were added and the reaction was stirred for another 2 h, then was concentrated in vacuo and adjusted to pH ~3 with 1 N aq. HCl. The mixture was extracted with EtOAc (3×5 mL). The combined organic extracts were washed with brine, dried over MgSO₄, filtered and concentrated in vacuo to afford the title compound (23 mg, 92% yield) as a white solid. LCMS, [M−H]⁺=389.3. ¹H NMR (400 MHz, CDCl₃) δ 6.99 (d, J=15.9 Hz, 1H), 6.73-6.71 (m, 1H), 6.69 (d, J=1.6 Hz, 1H), 5.69 (d, J=15.9 Hz, 1H), 3.63 (s, 2H), 2.96 (s, 2H), 1.60 (s, 12H), 1.48 (s, 6H). HPLC-1: RT=12.4 min, purity=100%; HPLC-2: RT=10.6 min, purity=98.4%.

EXAMPLE 14

3-(4-(((2,2-Dimethyl-2,3-dihydrobenzofuran-7-yl)oxy)methyl)bicyclo[2.2.2]octan-1-yl)propanoic acid

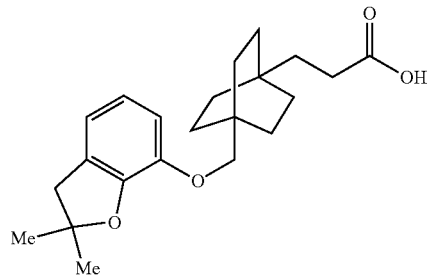 [SMILES: CC1(C)Cc2cccc(OCC34CCC(CCC(=O)O)(CC3)CC4)c2O1]

To a solution of (E)-3-(4-(((5-chloro-2,2-dimethyl-2,3-dihydrobenzofuran-7-yl)oxy)methyl)bicyclo[2.2.2]octan-1-yl)acrylic acid (10 mg, 0.026 mmol) in 1.5 mL EtOAc under Ar was added Pd/C (3 mg, 2.82 μmol). The reaction mixture was degassed and charged with a H₂-filled balloon and stirred for 40 h. The mixture was filtered through CELITE®, and the filtrate was concentrated in vacuo to afford the title compound (8 mg, 85% yield) as a white solid. LCMS, [M−H]⁺=357.4. ¹H NMR (400 MHz, CDCl₃) δ 6.78-6.67 (m, 3H), 3.65 (s, 2H), 3.00 (s, 2H), 2.33-2.24 (m, 2H), 1.60-1.46 (m, 14H), 1.44-1.36 (m, 6H). HPLC-1: RT=11.6 min, purity=100%; HPLC-2: RT=9.8 min, purity=100%.

EXAMPLE 15

3-(4-(((5-Chloro-2,2-dimethyl-2,3-dihydrobenzofuran-7-yl)oxy)methyl)bicyclo[2.2.2]octan-1-yl)propanoic acid

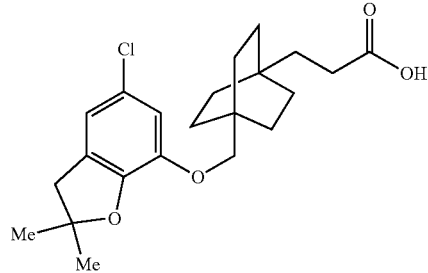

To a solution of (E)-3-(4-(((5-chloro-2,2-dimethyl-2,3-dihydrobenzofuran-7-yl)oxy)methyl)bicyclo[2.2.2]octan-1-yl)acrylic acid (4 mg, 10.23 μmol) in 1.5 mL MeOH/THF (1:1) under Ar was added Pt(IV) oxide (1.162 mg, 5.12 μmol). The reaction mixture was degassed, charged with a H₂ balloon and stirred for 30 min. The mixture was filtered through CELITE®, and concentrated in vacuo to afford the title compound (4 mg, 100% yield) as a white solid. LCMS, [M−H]⁺=393.4. ¹H NMR (400 MHz, CDCl₃) δ 6.73-6.70 (m, 1H), 6.69 (d, J=1.6 Hz, 1H), 3.61 (s, 2H), 2.96 (s, 2H), 2.33-2.26 (m, 2H), 1.59-1.46 (m, 14H), 1.45-1.37 (m, 6H). HPLC1:RT=12.8 min, purity=100%; HPLC-2: RT=11.1 min, purity=100%.

What is claimed is:

1. A compound of Formula (I):

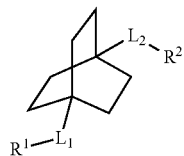
(I)

or a stereoisomer, a tautomer, or a pharmaceutically acceptable salt thereof, wherein:
- $L_1$ is $L_4$-O or O-$L_4$;
- $L_2$ is a hydrocarbon linker substituted with 0-2 $R^c$ or a hydrocarbon-heteroatom linker substituted with 0-2 $R^c$; wherein said hydrocarbon linker has one to six carbon atoms and may be straight or branched, saturated or unsaturated; and said hydrocarbon-heteroatom linker has one to four carbon atoms and one group selected from O, —CO—, S, —SO—, —$SO_2$—, NH and N($C_{1-4}$ alkyl);
- $L_4$ is a bond or a hydrocarbon linker; wherein said hydrocarbon linker has one to four carbon atoms and may be straight or branched;
- $R^1$ is selected from: $C_{6-10}$ carbocycle and a 5- to 10-membered heterocycle comprising carbon atoms and 1-4 heteroatoms selected from N, $NR^b$, O, and $S(O)_p$; wherein said carbocycle and heterocycle are substituted with 0-4 $R^3$ and 0-1 $R^4$;
- $R^2$ is selected from: $CO_2H$ and —$CONHSO_2(C_{1-4}$ alkyl);
- $R^3$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, and $NO_2$;
- $R^4$ is independently -$L_3$-$R^5$;
- $L_3$ is independently selected from: a bond, O, and C(=O);
- $R^5$ is independently selected from: phenyl and a 5- to 6-membered heteroaryl comprising carbon atoms and 1-4 heteroatoms selected from N, $NR^b$, O, and $S(O)_p$; wherein each ring moiety is substituted with 0-2 $R^a$;
- $R^a$, at each occurrence, is independently selected from: halogen, $C_{1-4}$ alkyl, $C_{1-4}$ alkoxy, and $C_{1-4}$ haloalkyl;
- $R^b$, at each occurrence, is independently selected from: H, $C_{1-4}$ alkyl, and —$(CH_2)_{0-2}$-(phenyl substituted with 0-3 $R^d$);
- $R^c$, at each occurrence, is independently selected from: halogen, OH, $C_{1-4}$ alkyl, $C_{1-4}$ haloalkyl, and $C_{1-4}$ alkyoxy;
- $R^d$, at each occurrence, is independently selected from: halogen, $C_{1-4}$ alkyl, $C_{1-4}$ alkoxy, and $C_{1-4}$ haloalkyl; and
- p is, independently at each occurrence, selected from 0, 1, and 2.

2. A compound according to claim 1, wherein:
- $L_1$ is $L_4$-O or O-$L_4$;
- $L_2$ is a hydrocarbon linker substituted with 0-1 $R^c$ or a hydrocarbon-heteroatom linker substituted with 0-1 $R^c$; wherein said hydrocarbon linker has one to six carbon atoms and may be straight or branched, saturated or unsaturated; and said hydrocarbon-heteroatom linker has one to four carbon atoms and one group selected from O, —CO— and S;
- $R^1$ is selected from: phenyl, indanyl, naphthyl, and a 5- to 10-membered heterocycle comprising carbon atoms and 1-4 heteroatoms selected from N, $NR^b$, O, and $S(O)_p$;

wherein each ring moiety is substituted with 0-4 $R^3$ and 0-1 $R^4$; and
- $R^4$ is selected from: thienyl, oxadiazolyl, and -$L_3$-phenyl; wherein each ring moiety is substituted with 0-2 $R^a$.

3. A compound according to claim 1, wherein the compound is of Formula (II):

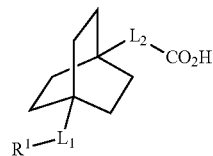
(II)

or a stereoisomer, a tautomer, or a pharmaceutically acceptable salt thereof, wherein:
- $L_1$ is $L_4$-O or O-$L_4$;
- $L_2$ is a hydrocarbon linker or a hydrocarbon-heteroatom linker; wherein said hydrocarbon linker has one to five carbon atoms and may be straight or branched, saturated or unsaturated; and said hydrocarbon-heteroatom linker has one to five carbon atoms and may be straight or branched, and has one to three carbon atoms and one O;
- $L_4$ is a bond or $CH_2$;
- $R^1$ is selected from:

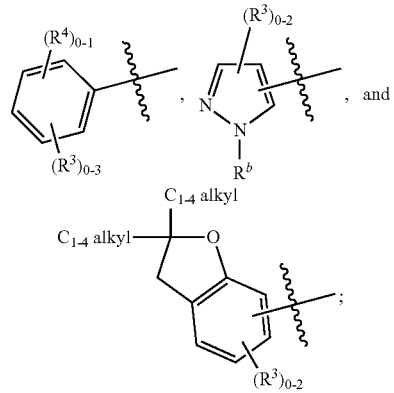

- $R^3$, at each occurrence, is independently selected from: $NO_2$, halogen, $C_{1-4}$ alkyl, $C_{1-4}$ alkoxy, $C_{1-4}$ alkylthio, $C_{1-4}$ haloalkyl, $C_{1-4}$ haloalkoxy, and $C_{1-4}$ haloalkylthio;
- $R^4$ is selected from: thienyl, oxadiazolyl, and -$L_3$-phenyl; wherein each ring moiety is substituted with 0-2 $R^a$;
- $L_3$ is independently a bond, O or C(=O);
- $R^a$, at each occurrence, is independently selected from: halogen and $C_{1-4}$ alkyl; and
- $R^b$ is independently phenyl substituted with 0-2 halo.

4. A compound according to claim 1, wherein:
- $L_2$ is selected from: $CH_2CH_2$, $CH_2CH_2CH_2$, CH=CH, $CH_2OCH_2$; and
- $R^1$ is independently selected from:

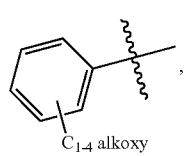

-continued

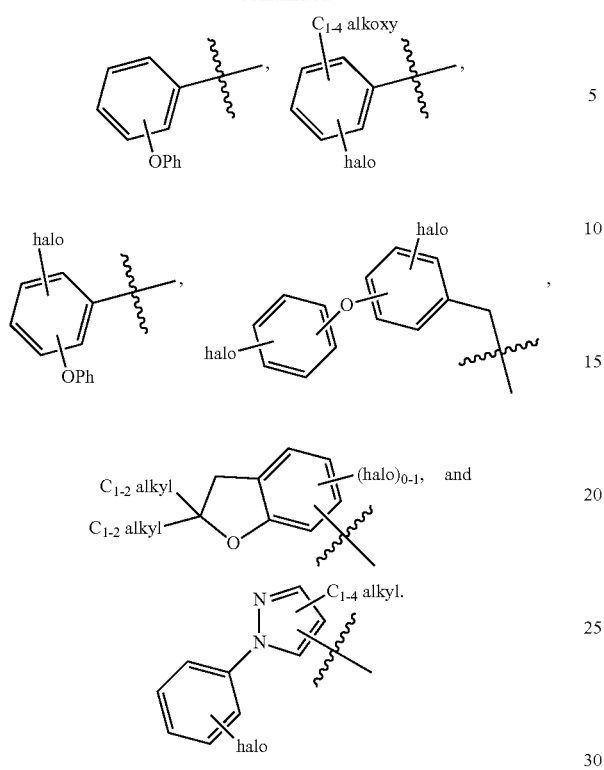

5. A compound according to claim 1, wherein:
R¹-L₁- is independently selected from:

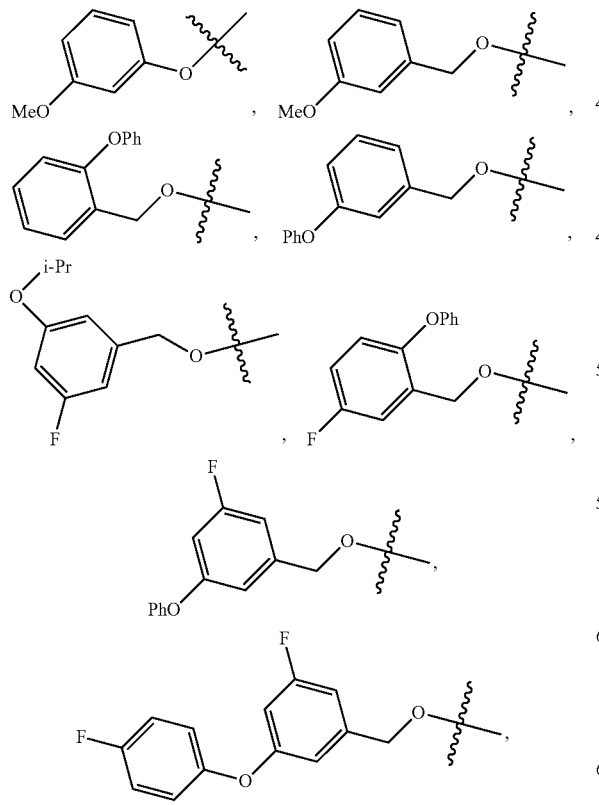

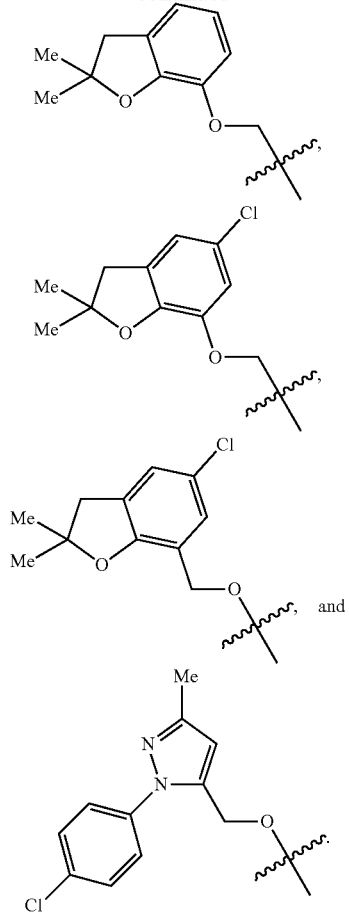

6. A compound according to claim 1, wherein the compound is selected from
- 3-(4-((5-Chloro-2,2-dimethyl-2,3-dihydrobenzofuran-7-yl)methoxy)bicyclo[2.2.2]octan-1-yl)propanoic acid;
- 4-(4-((5-Chloro-2,2-dimethyl-2,3-dihydrobenzofuran-7-yl)methoxy)bicyclo[2.2.2]octan-1-yl)butanoic acid;
- 3-(4-((1-(4-Chlorophenyl)-3-methyl-1H-pyrazol-5-yl)methoxy)bicyclo[2.2.2]octan-1-yl)propanoic acid;
- 3-(4-(3-Phenoxybenzyloxy)bicyclo[2.2.2]octan-1-yl)propanoic acid;
- 3-(4-(2-Phenoxybenzyloxy)bicyclo[2.2.2]octan-1-yl)propanoic acid;
- 4-(4-(3-Methoxybenzyloxy)bicyclo[2.2.2]octan-1-yl)butanoic acid;
- 3-(4-(3-Fluoro-5-phenoxybenzyloxy)bicyclo[2.2.2]octan-1-yl)propanoic acid;
- 3-(4-(5-Fluoro-2-phenoxybenzyloxy)bicyclo[2.2.2]octan-1-yl)propanoic acid;
- 2-((4-(3-Phenoxybenzyloxy)bicyclo[2.2.2]octan-1-yl)methoxy)acetic acid;
- 3-(4-(3-Fluoro-5-isopropoxybenzyloxy)bicyclo[2.2.2]octan-1-yl)propanoic acid;
- 3-(4-(3-Fluoro-5-(4-fluorophenoxy)benzyloxy)bicyclo[2.2.2]octan-1-yl)propanoic acid;
- (E)-3-(4-(((5-Chloro-2,2-dimethyl-2,3-dihydrobenzofuran-7-yl)oxy)methyl)bicyclo[2.2.2]octan-1-yl)acrylic acid;
- 3-(4-(((2,2-Dimethyl-2,3-dihydrobenzofuran-7-yl)oxy)methyl)bicyclo[2.2.2]octan-1-yl)propanoic acid;

3-(4-(((5-Chloro-2,2-dimethyl-2,3-dihydrobenzofuran-7-yl)oxy)methyl)bicyclo[2.2.2]octan-1-yl)propanoic acid;

or a stereoisomer, a tautomer, or a pharmaceutically acceptable salt thereof.

7. A pharmaceutical composition, comprising a pharmaceutically acceptable carrier and a compound of claim 1, or a stereoisomer, a tautomer, or a pharmaceutically acceptable salt thereof.

8. The pharmaceutical composition according to claim 7, further comprising one or more other suitable therapeutic agents selected from anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

9. The pharmaceutical composition according to claim 7, further comprising one or more other suitable therapeutic agents selected from: a dipeptidyl peptidase-IV inhibitor, a sodium-glucose transporter-2 inhibitor and a 11b-HSD-1 inhibitor.

* * * * *